(12) United States Patent
Lindh et al.

(10) Patent No.: US 9,309,517 B2
(45) Date of Patent: Apr. 12, 2016

(54) SELECTION OF RNA-APTAMERS AS ANTI-MALARIA AGENTS

(71) Applicant: APTAHEM AB, Malmo (SE)

(72) Inventors: Johan Lindh, Stockholm (SE); Tina Persson, Malmo (SE)

(73) Assignee: APTAHEM AB, Malmo (SE)

( * ) Notice: Subject to any disclaimer, the term of this patent is extended or adjusted under 35 U.S.C. 154(b) by 0 days.

(21) Appl. No.: 14/815,193

(22) Filed: Jul. 31, 2015

(65) Prior Publication Data

US 2016/0040164 A1 Feb. 11, 2016

Related U.S. Application Data

(62) Division of application No. 12/866,413, filed as application No. PCT/SE2009/000072 on Feb. 5, 2009, now Pat. No. 9,096,857.

(30) Foreign Application Priority Data

Feb. 5, 2008 (SE) ...................................... 0800262

(51) Int. Cl.
*C12N 15/115* (2010.01)

(52) U.S. Cl.
CPC .......... *C12N 15/115* (2013.01); *C12N 2310/16* (2013.01); *C12N 2310/3533* (2013.01)

(58) Field of Classification Search
None
See application file for complete search history.

(56) References Cited

U.S. PATENT DOCUMENTS 5,262,564 A 11/1993 Kun et al.
6,011,020 A 1/2000 Gold et al.

FOREIGN PATENT DOCUMENTS

WO 2004080420 9/2004

OTHER PUBLICATIONS

Normark et al. "PfEMP1-DBL1a Amino Acid Motifs in Severe Disease States of Plasmodium Falciparum Malaria", PNAS Oct. 2, 2007, vol. 104, No. 40, p. 15835-15840.
Lin et al. "Modified RNA Sequence Pools for in Vitro Selection", Nucleic Acids Research 1994, vol. 22, No. 24, p. 5229-5234.
Moll et al. "Generation of Cross-Protective Antibodies Against Plasmodium Falciparum Sequestration by Immunization with an Erythrocyte Membrane Protein 1-Duffy Binding-like 1a Domain", Infection and Immunity Jan. 2007, vol. 75, No. 1, p. 211-219.
Krause et al. "Characterization of the Antibody Response Against Plasmodium Falciparum Erythrocyte Membrance Protein 1 in Human Volunteers", Infection and Immunity Dec. 2007, vol. 75, No. 12, p. 5967-5973.
Ulrich et al. "In Vitro Selection of RNA Aptamers That Bind to Cell Adhesion Receptors of Trypanosoma Cruzi and Inhibit Cell Invasion", The Journal of Biological Chemistry Jun. 2002, vol. 277, No. 23, p. 20756-20762.
Lee et al. "Aptamer Therapeutics Advance", Current Opinion in Chemical Biology 2006, vol. 10, p. 282-289.
Hjalmarsson et al. "Aptamers—Future Tools for Diagnostics and Therapy", FOI Swedish Defence Research Agency, FOI-R-1216--SE, Apr. 2004, ISSN 1650-1942 Scientific Report, 41 Pages.
Jayasena, "Aptamers: An Emerging Class of Molecules That Rival Antibodies in Diagnostics", Clinical Chemistry 1999, vol. 45, No. 9, p. 1628-1650.
Eaton et al. "Post-SELEX Combinatorial Optimization of Aptamers", Bioorganic and Medicinal Chemistry 1997, vol. 5, No. 6, p. 1087-1096.
Chen et al. "Immunization with PfEMP1-DBL1a Generates Antibodies that Disrupt Rosettes and Protect Against the Sequestration of Plasmodium for Falciparum-Infected Erythrocytes", Vaccine 2004, vol. 22, p. 2701-2712.
Bradford, "A Rapid and Sensitive Method for the Quantitation of Microgram Quantities of Protein Utilizing the Principle of Protein-Dye Binding", Analytical Biochemistry 1976, vol. 72, p. 248-254.
Jellinek et al. "Potent 2'-Amino-2'-Deoxypyrimidine RNA Inhibitors of Basic Fibroblast Growth Factor", Biochemistry 1995, vol. 34, p. 11363-11372.
Pagratis et al. "Potent 2'-Amino-, and 2'-Fluoro-2'-Deoxyribonucleotide RNA Inhibitors of Keratinocyte Growth Factor", Nature Biotechnology Jan. 1997, vol. 15, p. 68-73.
Goringer et al. "In Vitro Selection of High-Affinity Nucleic Acid Ligands to Parasite Target Molecules", International Journal for Parasitology 2003, vol. 33, p. 1309-1317.
Chen et al. "Aptamer from Whole-Bacterium SELEX as new Therapeutic Reagent Against Virulent Mycobacterium Tuberculosis", Biochemical and Biophysical Research Communications 2007, vol. 357, p. 743-748.
Tucker et al. "Detection and Plasma Pharmacokinetics of an Anti-Vascular Endothelial Growth Factor Oligonucleotide-Aptamer (NX1838) in Rhesus Monkeys", Journal of Chromatography B. 1999, vol. 732, p. 203-212.
Kubik et al. "Isolation and Characterization of 2'Fluoro-, 2'-Amino-, and 2'-Fluoro-/Amino-Modified RNA Ligands to Human IFN-? That Inhibit Receptor Binding", The Journal of Immunology 1997, vol. 159, p. 259-267.
Conrad et al. "Detecting Immobilized Protein Kinase C Isozymes With RNA Aptamers", Analytical Biochemistry 1996, vol. 242, p. 261-265.
Martin et al. "Comparative Studies of UV-Induced DNA Cleavage by Structural Isomers of an Iodinated DNA Ligand", Int. J. Radiation Oncology Biol. Phys. 1994, vol. 29, No. 3, p. 549-553.
Potyrailo et al. "Adapting Selected Nucleic Acid Ligands (Aptamers) to Biosensors", Anal. Chem. 1998, vol. 70, p. 3419-3425.
Drolet et al. "Pharmacokinetics and Safety of an Anti-Vascular Endothelial Growth Factor Aptamer (NX1838) Following Injection into the Vitreous Humor of Rhesus Monkeys", Pharmaceutical Research 2000, vol. 17, No. 12, p. 1503-1510.
Barfod et al. Parasitol Res. 2009, vol. 105, p. 1557-1566, "In vitro selection of RNA aptamers against a conserved region of the Plasmodium falciparum erythrocyte membrane protein 1."
Missailidis et al. Cancer Biotherapy & Radiopharmaceuticals 2007, vol. 22, No. 4, p. 453-468, "Aptamers as Novel Radiopharmaceuticals: Their Applications and Future Prospects in Diagnosis and Therapy."
Extended Search Report for PCT/SE2009/000072, Completed on Jul. 9, 2012, 9 Pages.

*Primary Examiner* — Jennifer Graser
(74) *Attorney, Agent, or Firm* — Brooks Kushman P.C.

(57) ABSTRACT

The present invention relates to an aptamer or an active fragment thereof raised against the semi-conserved duffy binding ligand domain 1α, DBL1α, region of the *Plasmodium falciparum* erythrocyte membrane protein 1, PfEMPI, which aptamer has an effect against malaria, in particular severe cerebral malaria.

4 Claims, 8 Drawing Sheets

SELECTION OF RNA-APTAMERS AS ANTI-MALARIA AGENTS

CROSS-REFERENCE TO RELATED APPLICATIONS

Figure 1:
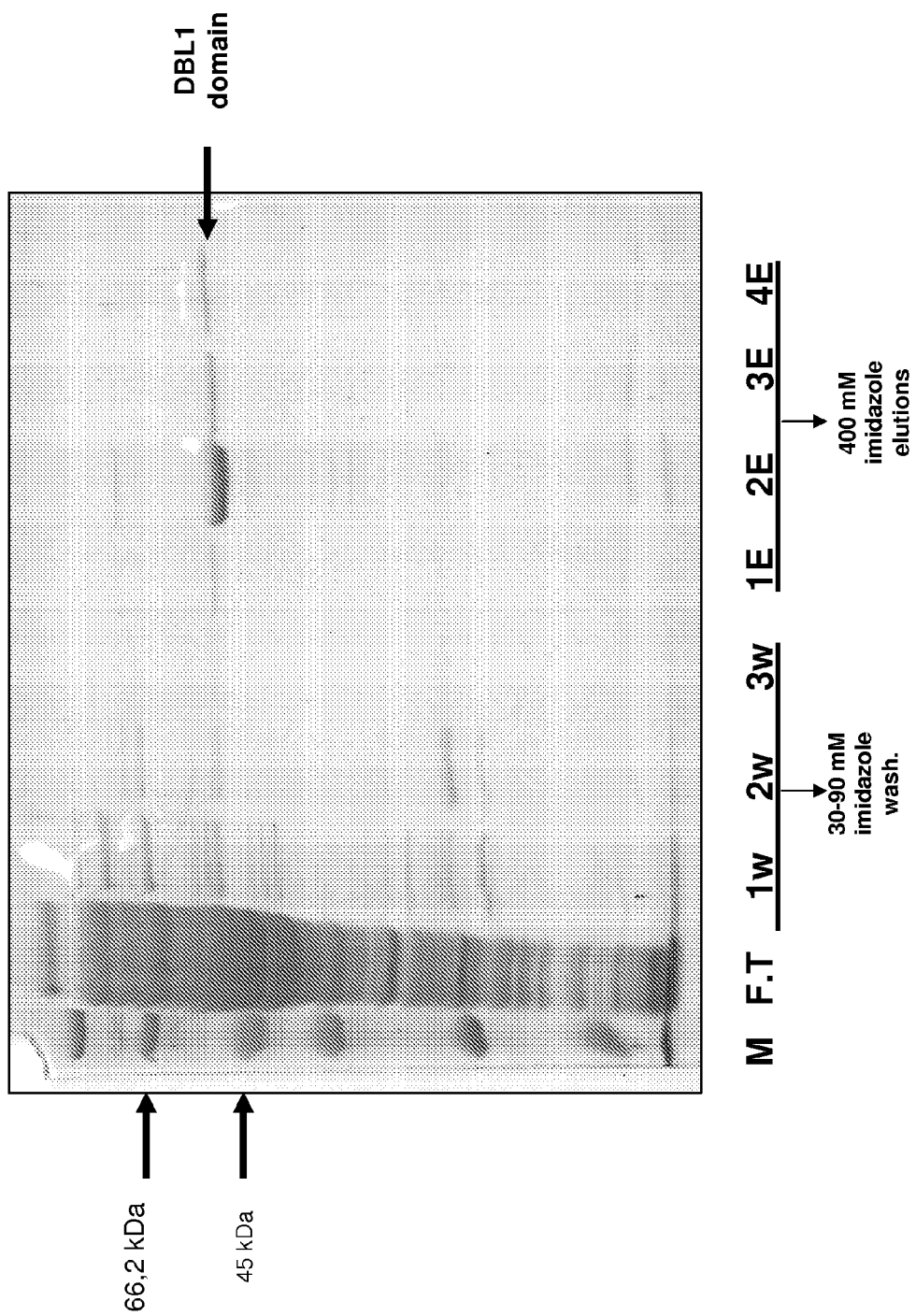

This application is a division of U.S. application Ser. No. 12/866,413 filed Sep. 17, 2010, which issued as U.S. Pat. No. 9,096,857 on Aug. 4, 2015, the disclosure of which is hereby incorporated in its entirety by reference herein.

SEQUENCE LISTING

The text file 2013_07_08_SequenceListing_MSK_ST25_revised.txt created Oct. 13, 2015, and of size 27 KB, filed herewith, is hereby incorporated by reference.

TECHNICAL FIELD

The present invention relates to particular RNA-aptamers against a conserved region of the *Plasmodium falciparum* erythrocyte membrane protein 1 (PfEMP1) to be used as an anti-malaria agent. Further, the invention relates to the use of such aptamers for the diagnosis of severe contra less severe malaria.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies ("mAbs"), are capable of specifically binding to selected targets and modulating the target's activity or binding interactions, e.g., through binding aptamers may block their target's ability to function. Discovered by an in vitro selection process from pools of random sequence oligonucleotides, aptamers have been generated for over 130 proteins including growth factors, transcription factors, enzymes, immunoglobulins, and receptors. A typical aptamer is 10-15 kDa in size (20-45 nucleotides), binds its target with nanomolar to sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties, in addition, they offer specific competitive advantages over antibodies and other protein biology, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated therapeutically acceptable toxicity and lack of immunogenicity. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et ah, J. Chromatography B. 732: 203-212, 1999)). With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologies and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders.

Furthermore, the aptamer discovery process readily permits lead modification, such as aptamer sequence optimization and the minimization of aptamer length [Conrad et al. 1996, Eaton et al. 1997]. Additionally, 2' modifications such as 2'-fluoro and 2'-O-Me may be utilized for stabilization against nucleases without compromising the aptamer binding interaction with the target. See e.g. Lin et a. Nucleic Acids Res. 22, 5229-5234 (1994); Jellinek et [alpha]l, Biochemistry 1995, 34, 11363-1137; Lin et [alpha]l, Nucleic Acids Res., 1994, 22, 5229-5234; Kubik et [alpha]l., J Immunol., 1997, 159(1), 259-267; and Pagratis et [alpha]l., Nat. Biotechnol., 1997, 1, 68-73.

Severe malaria is almost exclusively caused by *P. falciparum* infection and usually arises 6-14 days after infection. Consequences of severe malaria include coma and death if untreated—young children and pregnant women are especially vulnerable. Splenomegaly (enlarged spleen), severe headache, cerebral ischemia, hepatomegaly (enlarged liver), hypoglycemia, and hemoglobinuria with renal failure may occur. Renal failure may cause blackwater fever, where hemoglobin from lysed red blood cells leaks into the urine. Severe malaria can progress extremely rapidly and cause death within hours or days. In the most severe cases of the disease fatality rates can exceed 20%, even with intensive care and treatment. In endemic areas, treatment is often less satisfactory and the overall fatality rate for all cases of malaria can be as high as one in ten. Over the longer term, developmental impairments have been documented in children who have suffered episodes of severe malaria.

*Plasmodium falciparum* is the causative agent of severe malaria in humans. Millions of people worldwide are infected every year by *P. falciparum* and more than one million die, most of them small children in sub-Saharan Africa. The choice of drugs for malaria treatment has in the past primarily been quinine and chloroquine and since the 1960s sulfadoxine/pyrimethamine (SP). Unfortunately parasite resistance towards all these drugs has been documented in endemic regions. The most efficient drug used today as a first-line treatment is artemisinin and its derivates. Although no clinical resistance towards artemisinin has been demonstrated, there are indications of a developed in vitro resistance towards the drug in *P. falciparum*. Non-sterile immunity against severe malaria in residents in endemic regions has been described. This indicates the existence of antigenic homogeneity in the parasites causing severe malaria.

The protein known to be responsible for severe cerebral malaria by the process of rosetting and endothelial adherence is the erythrocyte membrane protein 1 (PfEMP1) expressed on the surface of the infected erythrocyte. Exposed on the infected erythrocyte it binds to a number of human cell surface receptors such as heparin sulphate, ICAM-1, CD36, CSA, enabling the parasite to adhere to the endothelial linings of small blood vessels (cytoadherence) as well as to non-infected erythrocytes (rosetting), thus preventing spleenic clearance from the bloodstream. Such sequestered parasites cause considerable obstruction to tissue perfusion.

PfEMP1 consist mainly of duffy binding ligand domains (DBL's) and cysteine rich inter domain regions (CIDR's), and the number of domains and size of the protein varies depending on which of the 60 var-genes is expressed. The fact that the parasite regularly changes the expressed var-gene and thus generating antigenic variation of the infected erythrocyte surface facilitates parasite avoidance of host immune system. Certain sequence conservation is though expected due to the adhesive function of this protein. The virulence-associated phenotype, rosetting, is mediated by the N-terminal Duffy-binding-like domain (DBL1alfa) which has a high degree of sequence conservation among the PfEMP1 domains. The definitive structure of DBL1α is not known though extensive modelling on domains with similar structure has been performed. This makes DBL1 an attractive candidate for the development of novel drugs against severe malaria. Attempts of antibody recognition of the structural conserved epitopes in DBL1α have been made without greater success due to the fact that the conserved regions are somewhat masked by the variable ones making them inaccessible to the comparatively large antibody.

Chen, Q. et al, Vaccine 22, (2004) p. 2701-2712 discloses that Immunization with PfEMP1-DBL1α generates antibodies that disrupt rosettes and protect against sequestration of *Plasmodium falciparum*-infected erythrocytes. The use of the PfEMP1-DBL1α protein to produce antibodies is a secondary therapeutic treatment, while the market asks for a direct therapeutic agent and method.

Moll, K. et al, Inf. Imm. vol. 75(1), (January 2007), p. 211-219 discloses generation of cross-protective antibodies against *Plasmodium falciparum* sequestration by immunization with an erythrocyte membrane protein 1-duffy binding like 1α domain. Also this work deals with the use of the PfEMP1-DBL1α protein to produce antibodies is a secondary therapeutic treatment, while the market asks for a direct therapeutic agent and method.

Based on these characteristics the present inventors designed a Systematic Evolution of Ligand by Exponential Enrichment (SELEX) protocol, which could be designed to allow the selection of RNA aptamers to bind with high affinity and specificity to the structurally conserved parts of DBL1α.

Ulrich, H. et al, J. Biol. Chem, vol. 277 (2002), p. 20756-20762 describes the SELEX method for in vitro selection of RNA aptamers that bind to cell adhesion receptors *Trypanosoma cruzi* and inhibit cell invasion.

A similar strategy has been reported for other pathogenic parasites where aptamers have successfully been selected against virulent surface proteins. In one reported case high affinity RNA aptamers were selected against the variable surface glycoprotein (VSG) of *Trypanosoma brucei* that proved to be capable of directing antibodies to the surface of live trypanosomes. The other reported study used a different approach. The selection was not performed using expressed surface proteins from *Trypanosoma cruzi* but using a displacement technique with 4 different human surface receptors (Ulrich , H. et al, supra).

*Trypanosoma cruzi* causes heart problems in the chronic stage, whereby treatment involves managing the clinical manifestations of the disease. For example, pacemakers and medications for irregular heartbeats may be life saving for some patients with chronic cardiac disease, while surgery may be required for megaintestine. The disease cannot be cured in this phase, however. Chronic heart disease caused by Chagas disease is now a common reason for heart transplantation surgery. Until recently, however, Chagas disease was considered a contraindication for the procedure, since the heart damage could recur as the parasite was expected to seize the opportunity provided by the immunosuppression that follows surgery.

Aptamers have been shown to present the same high specificity and affinity for their targets as antibodies. In addition to efficient binding, aptamers also display an inhibitory activity of their targets. The SELEX method is based on an iterative process of repeating steps of in vitro selection cycles where the initial DNA/RNA library of $10^{14}$-$10^{15}$ different molecules is reduced to a smaller pool of approximately 100 different molecules that have high affinity towards the target in question.

Lee, J. F., et al, Curr Opi. Chem. Biol. (2006), 10:282-289 is a review over aptamer therapeutics advance. Thereby anti-HIV-1, anti-VEGF, anti-RET, anti-theophylline, and anti-tenascin-C aptamers are discussed.

Hjalmarsson, K. et al, FOI-R-1216-SE (ISSN 1650-1942) discusses Aptamers—Future tools for diagnostics and therapy, and is in particular related to the SELEX-methodoly. An overview of different aptamers and their optional use is given.

Göringer, H. U., et al, Int. J. Parasit. 33 (2003), 1309-1317 discloses in vitro selection of high-affinity nucleic acid ligands to parasite target molecules, and discusses malaria, whereby the authors concluded primarily that the process of development has been slow because of the random screening methods of components have not been successful at identifying anti-parasitic compounds. The authors concentrate of discussing the SELEX protocol. Although malaria is a first parasite to be mentioned there is no hint that it adverse effects can be treated using an aptamer, but the authors discuss *Trypanosoma bruzei* causing sleeping sickness.

Normark, J. et al, PNAS, (2007) vol. 104, p. 15835-15840 discloses that PfEMP1-DBL1α amino acid motifs are preent in severe disease states of *Plasmodium falciparum* malaria. The paper does not discuss aptamers as potential agents in the treatment of severe malaria caused by *Plasmodium falciparum* but discusses raising of antibodies as a possible regime.

Krause, D. R. et al, Inf. Imm. vol 75, (2007) p. 5967-5973 discloses antibody response against *Plasmodium falciparum* and discusses that serum from a volunteer inhibits resetting. The authors state that "the diversity of this protein (PfEMP1) within and between parasites combined with antigenic switching between variants makes studying the development of PfEMP1-specific immunity difficult.

WO 2004/080420 to Mota et al discloses in general terms a methods for preventing or inhibiting the activity of malaria in vivo by administering an antimalarial agent to a mammal in need thereof, and indicates a number of different pathways to become interfered. In particular the disclosure discusses MET inhibition, MET being the receptor for Hepatocyte Growth Factor. The disclosure even mentions aptamers without any specification. In general the disclosure is very conceptual without delivering any specific solutions, but only thoughts about possible routes for treating malaria.

Jayasena, S. D. Clin. Chem. 45:9 (1999) p. 1628-1650 discloses Aptamers as an emerging class of molecules that rival antibodies in diagnostics. However, the disclosure gives no indication of therapeutic aptamers for treating malaria.

The present inventors further show that these specific high affinity binding aptamers are able to bind to PfEMP1 on the surface of live parasite and, lastly, that they have the capacity to disrupt rosettes. Herein it will be demonstrated specific binding of a set of aptamers that have an effect in vitro in formation of rosettes. It is further proposed to use these aptamers to diagnose the presence or not of severe malaria, i.e., to discriminate between light (or rather less severe forms) and severe forms of malaria.

SUMMARY OF THE PRESENT INVENTION

Thus the present invention relates to certain RNA-aptamers or active fragments thereof raised against PfEMP1 as an anti-malarian agent.

DETAILED DISCLOSURE OF THE PRESENT INVENTION

In particular the present invention relates to certain RNA-aptamers raised against the semi-conserved dully binding ligand domain 1α, DBL1α, region of the *Plasmodium falciparum* erythrocyte membrane protein 1, PfEMP1.

In a preferred embodiment thereof the invention relates to an aptamer selected from the group consisting of

```
                                                  (SEQ. ID. NO. 1)
UGCCAACCUUCGAUGCAAGAUAAUACUUUUGAUGGUGUAGUCGUAUUGUU (SEQ. ID. NO. 2)
UCAUGUGCCAGUGUUUGAAAAAACGCGUUGAUUGCUGGUGUGGUGAGCUA

GU, (SEQ. ID. NO. 3)
CUUCGAACGGCCCUGGUUGUUGGUUUUAAUUCAUUUAUCCGCGUGGUCAC

GGU, (SEQ. ID. NO. 4)
UAGCUCACCACACCAGCAAUCAACGCGUUUUUUCAAACACUGGCACAUGA (SEQ. ID. NO. 5)
AACAAUACGACUACACCAUCAAAAGUAUUAUCUUGCAUCGAAGGUUGGCA,
and (SEQ. ID. NO. 6)
GUGACCACGCGGAUAAAUGAAUCAAAAACAACAACCAGGGCCGUUCGACU

ACGCUAAUUAUCCCG
``` or an active fragment thereof.

In a preferred embodiment thereof the invention relates to an aptamer having the sequence

```
GACUGAUUACGCCAGCUUGG                    (SEQ. ID. NO. 23)
or

GAC^F U^F GAU^F U^F AC^F GC^F C^F AGC^F U^F U^F GG    (SEQ. ID. NO. 24)
```

In a further preferred embodiment thereof the invention relates to an aptamer selected from the group consisting of fluorinated aptamers consisting of

```
                                                                (SEQ. ID. NO. 7)
U^F GC^F C^F AAC^F C^F U^F U^F C^F GAU^F GC^F AAGAU^F AAU^F AC^F U^F U^F U^F U^F GAU

^F GGU^F GU^F AGU^F C^F GU^F AU^F U^F GU^F U^F , (SEQ. ID. NO. 8)
U^F C^F AU^F GU^F GC^F C^F AGU^F GU^F U^F U^F GAAAAAAC^F GC^F GU^F U^F GAU^F U^F G

C^F U^F GGU^F GU^F GGU^F GAGC^F U^F AGU^F
and (SEQ. ID. NO. 9)
C^F U^F U^F C^F GAAC^F GGC^F C^F C^F U^F GGU^F U^F GU^F U^F GGU^F U^F U^F U^F AAU^F U^F

C^F AU^F U^F U^F AU^F C^F C^F GC^F GU^F GGU^F C^F AC^F GGU^F , (SEQ. ID. NO. 10)
U^F AGC^F U^F C^F AC^F C^F AC^F AC^F C^F AGC^F AAU^F C^F AAC^F GC^F GU^F U^F U^F U^F

U^F U^F C^F AAAC^F AC^F U^F GGC^F AC^F AU^F GA (SEQ. ID. NO. 11)
AAC^F AAU^F AC^F GAC^F U^F AC^F AC^F C^F AU^F C^F AAAAGU^F AU^F U^F AU^F C^F U^F

U^F GC^F AU^F C^F GAAGGU^F U^F GGC^F A (SEQ. ID. NO. 12)
GU^F GAC^F C^F AC^F GC^F GGAU^F AAAU^F GAAU^F C^F AAAAAC^F AAC^F AAC^F C^F A

GGGC^F C^F GU^F U^F C^F GAC^F U^F AC^F GC^F U^F AAU^F U^F AU^F C^F C^F C^F G
``` or an active fragment thereof.

Another aspect of the invention relates to the use of one or more aptamers, or an active fragment thereof, raised against the semi-conserved duffy binding ligand domain 1α, DBL1α, region of the *Plasmodium falciparum* erythrocyte membrane protein 1 (PfEMP1) in the treatment of cerebral malaria.

In a preferred embodiment thereof the invention relates to the aptamer is selected from the group consisting of

```
                                                  (SEQ. ID. NO. 1)
UGCCAACCUUCGAUGCAAGAUAAUACUUUUGAUGGUGUAGUCGUAUUGUU (SEQ. ID. NO. 2)
UCAUGUGCCAGUGUUUGAAAAAACGCGUUGAUUGCUGGUGUGGUGAGCUA

GU, (SEQ. ID. NO. 3)
CUUCGAACGGCCCUGGUUGUUGGUUUUAAUUCAUUUAUCCGCGUGGUCAC

GGU, (SEQ. ID. NO. 4)
TAGCTCACCACACCAGCAATCAACGCGTTTTTTCAAACACTGGCACATGA (SEQ. ID. NO. 5)
AACAATACGACTACACCATCAAAAGTATTATCTTGCATCGAAGGTTGGCA,
and (SEQ. ID. NO. 6)
GTGACCACGCGGATAAATGAATCAAAAACAACAACCAGGGCCGTTCGACT

ACGCTAATTATCCCG.
```

In a further preferred embodiment thereof the invention relates to the aptamer is selected from the group consisting of fluorinated aptamers consisting of (SEQ. ID. NO. 7)
$\mathrm{U^FGC^FC^FAAC^FC^FU^FU^FC^FGAU^FGC^FAAGAU^FAAU^FAC^FU^FU^FU^FU^FGA}$ $\mathrm{U^FGGU^FGU^FAGU^FC^FGU^FAU^FU^FGU^FU^F}$, (SEQ. ID. NO. 8)
$\mathrm{U^FC^FAU^FGU^FGC^FC^FAGU^FGU^FU^FU^FGAAAAAAC^FGC^FGU^FU^FGAU^FU^FG}$ $\mathrm{C^FU^FGGU^FGU^FGGU^FGAGC^FU^FAGU^F}$ (SEQ. ID. NO. 9)
$\mathrm{C^FU^FU^FC^FGAAC^FGGC^FC^FC^FU^FGGU^FU^FGU^FU^FGGU^FU^FU^FU^FAAU^FU^F}$ $\mathrm{C^FAU^FU^FU^FAU^FC^FC^FGC^FGU^FGGU^FC^FAC^FGGU^F}$ (SEQ. ID. NO. 10)
$\mathrm{U^FAGC^FU^FC^FAC^FC^FAC^FAC^FC^FAGC^FAAU^FC^FAAC^FGC^FGU^FU^FU^FU^F}$ $\mathrm{U^FU^FC^FAAAC^FAC^FU^FGGC^FAC^FAU^FGA}$ (SEQ. ID. NO. 11)
$\mathrm{AAC^FAAU^FAC^FGAC^FU^FAC^FAC^FC^FAU^FC^FAAAAGU^FAU^FU^FAU^FC^FU^F}$ $\mathrm{U^FGC^FAU^FC^FGAAGGU^FU^FGGC^FA}$ (SEQ. ID. NO. 12)
$\mathrm{GU^FGAC^FC^FAC^FGC^FGGAU^FAAAU^FGAAU^FC^FAAAAAC^FAAC^FAAC^FC^FA}$ $\mathrm{GGGC^FC^FGU^FU^FC^FGAC^FU^FAC^FGC^FU^FAAU^FU^FAU^FC^FC^FC^FG}$.

A still further aspect of the invention relates to a diagnosis tool for determining the presence of severe malaria, by determining the respsonse of a blood sample to an aptamer raised against the semi-conserved duffy binding ligand domain 1α, DBL1α, region of the *Plasmodium falciparum* erythrocyte membrane protein 1, PfEMP1.

A still further aspect of the invention relates to a method for prophylactically and/or therapeutically treating severe malaria by administering to a human being suffering therefrom or risking to suffer therefrom an therapeutically effective amount of an aptamer raised against the semi-conserved duffy binding ligand domain 1α, DBL1α, region of the *Plasmodium falciparum* erythrocyte membrane protein 1, PfEMP1.

The invention will be described in the following with reference to the experiments carried out. These experiments relates to the isolation of certain RNA-aptamers, as well as the biological effect of such certain RNA-aptamers on the resetting event.

Expression of DBL1α in *E.coli.*

Protein expression in *E. coli*. Recombinant DBL1$^{his}$ from FCR3S1.2 was expressed as follows, SG13009 (pREP4) cells from Qiagen harboring plasmids pQE-TriSystem His-Strep 2 (DBL1$^{his}$), or pQE-60 (DBL1$^{his}$) [22] were grown in LB-medium containing ampicillin (100 μg/mL) and kanamycin (30 μg/mL) at either 22° C. or 37° C. At $OD_{600}$=0.8 cells were induced with 0.1 mM IPTG for 3 h; 1 liter cell suspension was harvested (4° C., 25 min, 3000 g) and resuspended in 25 mL lysis buffer (50 mM $NaH_2PO_4$/NaOH pH 7.4, 300 mM NaCl, 1 mM PMSF (Sigma) 0.05% Triton x-100, 10 mM imidazole). Cells incubated with Lysozyme on ice for 30 min, and sonicated. Insoluble cell debris was removed by centrifugation (4° C. 30 min, 18.000 g). The supernatant was DNase treated and incubated with 1 mL Ni-NTA agarose beads (Qiagen) for 2 h at 4° C. with gentle agitation. Beads were pelleted at 100× g for 3 min. and washed 3 times with 15 mL wash buffer (50 mM $NaH_2PO_4$/NaOH pH 7.4, 300 mM NaCl, 0.05% Triton x-100, 30 mM Imidazole). Bound protein was eluted with 400 mM imidazole (Sigma), 50 mM $NaH_2PO_4$, 300 mM NaCl which was subsequently removed by dialysis against PBS buffer with 0.05% Triton X-100 for 18 h at 4° C. Protein purity was estimated by running samples on 10% SDS-PAGE and finally protein concentration was determined (Bradford 1976). Alternatively, His-tagged DBL1 was purified on FPLC. *E. coli* extracted soluble fraction was loaded onto Ni-column on FPLC (AmershamBiosciences) with a flow speed of 0.5 mL/min. Bound protein was washed with 5-70 mM Imidazole gradient (60 mL at 1 mL/min). Protein was eluted with 400 mM imidazole and analysed as previously described. All chemicals were obtained from Sigma.

The entire sequence of DBL1α from FCR3S1.2 (Moll K, Pettersson F, Vogt A M, Jonsson C, Rasti N, et al. (2007) Generation of cross-protective antibodies against *Plasmodium falciparum* sequestration by immunization with an erythrocyte membrane protein 1-duffy binding-like 1 alpha domain. Infect Immun 75: 211-219) was optimized with regard to codon-usage for expression in *E.coli*. By His-Tag high affinity purification soluble DBL1α was purified (FIG. 1). Verification of DBL1α$^{His}$ was confirmed with Western blot using His-Tag- or DBL1α specific antibodies. The recombinant domain has been analysed for "activity" by its affinity towards heparin, one of the major targets for DBL1α. The recombinant domain binds to heparin in both free form and on heparin columns.

Selection of DBL1α—Specific RNA Aptamers.

For the in vitro selection a combinatorial library of $5\times10^{14}$ randomly chosen RNA sequences was used. The library consisted of sequences that had a size of 50 nucleotides flanked by primer binding sites of 20 nucleotides resulting in RNA molecules of 90 nucleotides. T7 RNA transcription was carried out in the presence of 2'F-modified pyrimidine nucleotides to select serum-stable aptamers. The strategy was to enrich for aptamers that would have affinity towards the recombinant DBL1α domain from the high rosetting strain FCR3S1.2. Eight rounds of selection and amplification on DBL1α pre-bound to nickel beads was performed. The course of the experiment was monitored by determining the percentage of bound RNA in every SELEX round (FIG. 2). Increasing recovery of RNA was observed through the selection rounds and maximum binding was achieved in round 8 with approx. 58% RNA recovery. To avoid unspecific binding to the Ni-NTA agarose (Qiagen) matrix, a pre-selection on pure matrix was performed before each selection round. The amplified DNA pool from round 8 was cloned in a TA-vector, and the nucleotide sequences of 70 individual clones were determined. The bioinformatics data using MEME/MAST show a clustering of clones into several conserved groups.

Grouping of Sequenced Clones Using MEME/MAST.

The motif search resulted in a classification of the clones in several different conserved groups. The most conserved group (A) contained 6 members. Group (B) to (D) had statistically values whereas the last two large groups had a low degree of conservation. A lot of smaller but well conserved groups with 3-4 listed members were identified in the dataset. The right column in table 1 is the frequency of which the consensus sequence occurs within the 70 clones tested. Few clones such as g06 and g07 were divided into two groups (A and D). An interesting observation is detected when predicting the secondary structure using mfold (computer free software) on the randomised region of clones in the G-T rich group (E). These clones build rather stable structures with low ΔG values and melting points above 55° C. The clones of group (F) in contrary to the clones of group (E) have no stable secondary structures when mfold predictions were performed for the randomised region. Lastly a large number of orphans were present among the 70 clones.

TABLE 1

Isolated multilevel consensus sequences generated by MEME/MAST software on the 70 sequenced clones from the in vitro selection on DBL1α$^{His}$.

| (Group) and multilevel consensus sequence | MEME probability score | Occurrence |
|---|---|---|
| (A): GACTGATTACGCCAGCTTGG | (E = 7.9 × 10$^{-20}$) | 8.6% |
| (B): CACACTGGCGGCCGCTCGAG | (E = 2.0 × 10$^{-7}$) | 5.7% |
| (C): AATTCGCCCTTGCCG | (E = 3.9 × 10$^{-6}$) | 12.9% |
| (D): AGCTCGGATCCACTAATAA | (E = 1.6 × 10$^{-4}$) | 12.9% |
| (E): GTTGTTGGTTTGGCTTGTT | (E = 6.2 × 10$^{0}$) | 25.7% |
| (F): AACACCAACACCAACA | (E = 3.0 × 10$^{3}$) | 18.6% |

Testing individual aptamers on recombinant DBL1α$^{His}$. A substantial number of clones were tested for binding on DBL1α$^{His}$. Radioactive labelled clones were analysed for recovery on DBL1α$^{His}$ with unselected RNA from pool 0 as a negative control. In this manner the variation in binding affinity between different clones could be observed. Clones that displayed a higher degree of binding were used for further studies. The concentration of protein was 350-400 nM and RNA was 40 nM in the experiment displayed in FIG. 3. The clones b02, d12, eo5 had similar recovery level (70%) whereas unselected RNA from pool 0 had a recovery rate at 11.7%. Pool 8, which represent the finale SELEX selected pool had a recovery rate of 51%. Clone e11 had a lower recovery level than b02, d12, e05, indicating a lower binding affinity. Several other binding experiments were conducted (data not shown) and RNA recovery level on selected clones was in general lower than 70%, but always significantly higher (by a factor of 2-5) than unselected RNA. A conclusion from the conducted experiments was that the ratio between DBL1α$^{His}$ and RNA had the most profound effect on recovery level. RNA/DBL1α$^{His}$ at 1:9 generally resulted in high recovery rates, whereas RNA/DBL1α$^{His}$ at a ratio of 1:3 resulted in low levels of recovery (Selected Clones at 12-25% recoveries and unselected RNA at 1-4%). The clones, which showed higher recovery rates were chosen for Electrophoretic Mobility Shift Assays and tested in a live cell assay.

The nucleic acid sequences of the clones d12, b02, and e05, respectively, were determined and are represented by the following RNA sequences:

```
d12/1,2
                                        (SEQ. ID. NO. 1)
UGCCAACCUUCGAUGCAAGAUAAUACUUUGAUGGUGUAGUCGUAUUGUU (SEQ. ID. NO. 4)
UAGCUCACCACACCAGCAAUCAACGCGUUUUUCAAACACUGGCACAUGA b02/1,2
                                        (SEQ. ID. NO. 2)
UCAUGUGCCAGUGUUUGAAAAAACGCGUUGAUUGCUGGUGUGGUGAGCUA

GU (SEQ. ID. NO. 5)
AACAAUACGACUACACCAUCAAAAGUAUUAUCUUGCAUCGAAGGUUGGCA, e05/1,2
                                        (SEQ. ID. NO. 3)
CUUCGAACGGCCCUGGUUGUUGGUUUUAAUUCAUUUAUCCGCGUGGUCAC

GGU.

(SEQ. ID. NO. 6)
GUGACCACGCGGAUAAAUGAAUCAAAAACAACAACCAGGGCCGUUCGACU

ACGCUAAUUAUCCCG
```

To improve the half-life time and the stability of the aptamer in blood it can be fluorinated at one or more carbon atoms, preferably all carbon atoms. Of the aptamers disclosed above the following aptamers will then be obtained:

```
                                        (SEQ. ID. NO. 7)
U^FGC^FC^FAAC^FC^FU^FU^FC^FGAU^FGC^FAAGAU^FAAU^FAC^FU^FU^FU^FU^FGA

U^FGGU^FGU^FAGU^FC^FGU^FAU^FU^FGU^FU^F, (SEQ. ID. NO. 8)
U^FC^FAU^FGU^FGC^FC^FAGU^FGU^FU^FU^FGAAAAAAC^FGC^FGU^FU^FGAU^FU^FG

C^FU^FGGU^FGU^FGGU^FGAGC^FU^FAGU^F
and (SEQ. ID. NO. 9)
C^FU^FU^FC^FGAAC^FGGC^FC^FC^FU^FGGU^FU^FGU^FU^FGGU^FU^FU^FU^FAAU^FU^F

C^FAU^FU^FU^FAU^FC^FC^FGC^FGU^FGGU^FC^FAC^FGGU^F, (SEQ. ID. NO. 10)
U^FAGC^FU^FC^FAC^FC^FAC^FAC^FC^FAGC^FAAU^FC^FAAC^FGC^FGU^FU^FU^FU^F

U^FU^FC^FAAAC^FAC^FU^FGGC^FAC^FAU^FGA (SEQ. ID. NO. 11)
AAC^FAAU^FAC^FGAC^FU^FAC^FAC^FC^FAU^FC^FAAAAGU^FAU^FU^FAU^FC^FU^F

U^FGC^FAU^FC^FGAAGGU^FU^FGGC^FA (SEQ. ID. NO. 12)
GU^FGAC^FC^FAC^FGC^FGGAU^FAAAU^FGAAU^FC^FAAAAAC^FAAC^FAAC^FC^FA

GGGC^FC^FGU^FU^FC^FGAC^FU^FAC^FGC^FU^FAAU^FU^FAU^FC^FC^FC^FG
``` or an active fragment thereof.

Further, it is possible to obtain active fragments of the aptamers by eliminating part of each of the sequence above.

Electrophoretic Mobility Shift Assays

Figure 4:
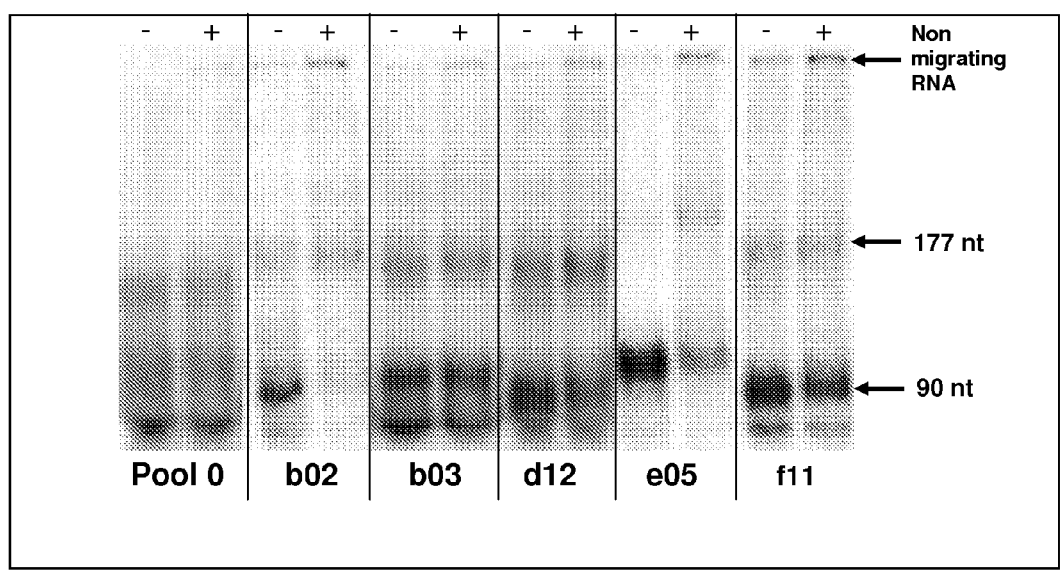

To study RNA/DBL1α$^{His}$ interaction in solution a number of EMSA experiments were conducted. The protein used for these experiments was freshly eluted from the Ni-NTA beads to avoid long storage and freezing in solution to prevent precipitation of DBL1α$^{His}$. The RNA was internally labelled with $^{32}$P-ATP and migration after incubation with DBL1α$^{His}$ or BSA was analysed on 10% native polyacrylamide gel. The upper band (177 nucleotide long RNA) seen in FIG. 4 is an incorrect product of the T7 transcription that is derived from a longer transcription template. This template is a product generated in the previous PCR reaction (binding of PCR primer to en external T7 site in the TOPO-vector). With the addition of DBL1α$^{His}$ to the RNA clone b02 and e05 the major product of 90 nt is decreased substantially, whereas the upper band (177 nt) remains unchanged, indicating that the 177 nt RNA molecule does not interact with DBL1α$^{His}$. Even clones d12 and to some degree f11, show a decrease in the 90 nt RNA molecule when incubated with DBL1α$^{His}$. b03, a clone that generally showed a low recovery rate in the in vitro binding to DBL1α$^{His}$ on Ni-NTA beads, shows a very little change in amount of 90 nt RNA. Throughout the EMSA experiments conducted, no real band shift was observed (RNA molecule bound to protein with slower migration). The major band shift of the 90 nt RNA seen in FIG. 5 for clone e05 did not migrate in the gel but was retained in the top of the gel beneath the loading well.

Aptamer Binding to Live Parasites.

In order to verify the surface binding of aptamers to live parasites, a live cell assay with fluorescein labelled aptamers was preformed. The fluorescein labelled nucleotides were co-transcriptionally incorporated into the RNA aptamers. The surface-bound aptamers were detected using fluorescence microscopy. The results are summarized in FIG. 6. As a control during this experiment, fluorescein labelled aptamer RNA from unselected pool 0 was used. These results show a significant association between specific single RNA aptamers as well as the selected RNA from pool 8 and the parasitized erythrocytes.

Effects of RNA Aptamers on Rosetting in FCR3S1.2 In Vitro

Since the live cell assay using fluorescein labelled RNA aptamers showed association to the infected erythrocyte, the next step was to analyse whether this interaction could affect the rosetting status of a blood culture of the highly rosetting and multi-adhesive clone FCR3S1.2. The rosetting and cytoadherence of FCR3S1.2 is sensitive to heparin and heparin sulphate and rosettes can be disrupted with an addition of 100 µg/mL heparin in a 5% hematocrit culture with 5% parasitimia. This disruption is believed to be caused by the competition between the DBL1α-bound heparin sulphate—like GAG and the added heparin in solution. In a similar fashion it was investigated whether the SELEX selected RNA aptamers can disrupt the interaction between DBL1α and GAG on the bound uninfected erythrocyte. The aptamers were tested in blood cultures at a concentration of 2 µg/mL (65 nM) to 12 µg/mL (387 nM), and with unselected RNA from pool 0 as a negative control. Total disruption was seen at 12 µg/mL for the clones b02, d12 and e05 and a decrease in rosette rate to 35% in relation to the control was observed at 8 µg/mL (258 nM) (FIG. 7 med rosette status as function of concentration). An effect could be seen at a concentration of 65 nM, as giant rosettes were decreased to smaller once (FIG. 8). RNA from pool 0 did not disrupt rosettes in this concentration range (65-387 nM), but a small degree of disruption (5-10% lower than untreated cells) was observed at an unselected RNA concentration of 650 nM to 850 nM. Stability of the 2'F modified aptamers in blood/serum culture was tested. After 3 hours incubation no apparent degradation was observed when running samples on 10% UREA-PAGE (data not shown). This correlates with previous work done with 2'F modified RNA in blood where the half-life of the RNA was approximately 15 hours.

It is generally accepted that severe malaria is most likely caused by sequestration of the infected erythrocytes, yet there is no specific anti-sequestration drug available today. PfEMP1 is a key molecule used by P. falciparum to interact with the human host in many ways. The adhesive function of this protein makes it possible for the parasite to adhere to endothelial lining, removing the parasitized erythrocyte from the peripheral circulation and hence avoid spleenic clearance.

An aptamer can bind its target with extremely high affinity and it has been suggested that they are even more specific than antibodies. Since antibodies must be produced biologically, which would involve expensive cell cultures and eventually animal models, aptamers have an apparent advantage since they can be produced completely in a test tube. Another advantage with the usage of aptamers compared with the use of specific antibodies is in the size difference. Due to their smaller size the RNA aptamers have great potential reaching more buried structures that antibodies are not able to access due to steric hindrance. Additionally the RNA aptamers are easy to chemically modify and elicit little or no immunogenicity in therapeutic applications. Through SELEX technique aptamers have been raised against the semi-conserved DBL1α region of PfEMP1. In this project it was focused on generating RNA-aptamers, testing the binding capacity of different RNA aptamers towards recombinant His-tag DBL1α and examine the capacity of rosette disruption. In a similar fashion in vitro selection with peptide- or single-chain antibody fragments using phage display technique on surface proteins of P. vivax P. falciparum has also been reported.

Producing the DBL1α target for selection proved to be a hard task. A trail of different optimizing experiments changing induction time, temperature and IPTG concentration was performed but none of the above mentioned factors seemed to have a dramatic effect on the yield. The amount of DBL1α$^{His}$ protein in solution was always fairly limited and most protein was found in the insoluble fraction. The quality assessment on purified protein from the soluble fraction has been tested through binding to the ligand heparin. Through eight selection rounds on recombinant DBL1α$^{His}$ major increase in RNA recovery was observed and to investigate for conserved motifs within the selected RNA, 70 clones were sequenced and analysed. Unfortunately the outcome of the MEME/MAST search revealed a large number of smaller conserved groups. A strategy to minimize the number of groups would have been to increase the selection pressure by decreasing the concentration of RNA and DBL1α$^{His}$ in later selection rounds, hence discarding RNA aptamers with poor affinity towards the target. The result would be a more homologous pool of RNA binders. Unfortunately the concentration of protein was kept at ~1 µM since the quality and solubility of DBL1α$^{His}$ after elution and dialysis showed to be poor. Another approach to increase affinity and more importantly obtain biological relevant aptamers would be to pan the DBL1α$^{His}$ selected aptamers on live infected erythrocytes. This approach was tested by incubating an enriched culture of FCR3S1.2 (70-80% parasitimia) with pool eight RNA and isolate surface bound RNA by trypsine digest. Results were though unsatisfying and this approach was discarded. The variation and large amount of orphans among the 70 sequenced clones could be a result of the "sticky" nature of DBL1α due to its heparin sulphate binding site and overall positive charge. RNA molecules while adopting a stable duplex hairpin structure with the addition of the negative charge nature of the RNA molecule could theoretically mimic the heparin molecule with its sugar backbone and negative sulphates in place of RNA's phosphate and in the same manner bind to the GAG binding domain of DBL1α with a low $K_D$ constant. Among the tested clones; b02, d12 and e05 seemed to be stable in regard of binding to DBL1α$^{His}$. These aptamers displayed association to the protein when incubated with DBL1α$^{His}$ at a concentration of 400 nM correlating with the results obtained during the EMSA experiments. At times the band shift observed in these experiments showed the RNA to be retained in the top part of the gel in the presence of DBL1α$^{His}$. It is believed that the RNA is bound to DBL in a large non-migrating complex due to the positive charge and low degree of solubility of the protein.

In order to verify if the RNA/protein binding had any biological relevance the three clones were fluorescein labelled and incubated with live FCR3S1.2 parasites. Fluorescein images were merged with images of the nuclei stained with DAPI. The results show the co-localisation between the fluorescein labelled RNA and the DAPI stained nuclei. The gathered results from this assay show a significant specificity between the selected aptamer clones and the surface of the infected erythrocyte compared to the association between unselected RNA and the infected erythrocyte. An alternative method for a fluorescence based live cell assay would be to end-label the 2'F modified aptamer with biotin thereby maintaining the modification on the UTP and CTP. This greatly enhances stability in blood/serum culture. Exchanging 2'F-d (CU)TP with (CU)TP could also impose a small conformational change in the RNA thereby decreasing the affinity compared to the original 2'F modified RNA. The 2'F atom could have a direct role in binding through interaction with amino acid residues in DBL1α. When conducting the live cell assay the rosettes are not manually disrupted prior to the addition of the aptamer. Rosetting could prevent the binding of the labelled aptamers to the DBL1α exposed on the surface as the protein is bound and the space occupied by the GAG molecule. Though if the aptamers have a higher affinity towards DBL1α than the GAG molecule, they might be able to compete with the binding and thereby exclude and disrupt the GAG/DBL1α interaction, visualised as disrupted rosettes. This was tested for the three SELEX selected clones b02, d12 and e05. They were all able to disrupt rosettes in an in vitro culture of FCR3S1.2. A concentration as low as 65 nM had a limited effect on the rosette rate per se, it did however have an apparent effect when it came to size decrease of the rosettes. If one should include the size of a rosette as the indicator of the rosette state in the culture the effect becomes much more apparent. At an aptamer concentration of 260 nM the rosette rate was decreased to approximately 35% of the control and a concentration of 387 nM was enough to completely disrupt rosettes to single infected erythrocytes with no bound erythrocytes. Unselected RNA did not have any effect at these concentrations but an increase to 650-850 nM showed a slight effect (5-10% disruption). The cause of this effect was never investigated. In case of heparin's ability to disrupt rosettes of FCR3S1.2 a reduction from 100% to 20% was observed at a concentration of 100 μg/mL in the work of vogt et al., which is approximately 7 μM (Heparin ~15 kDa). The selected RNA has the ability to disrupt rosettes at 15 times lower concentration than heparin. The clone e02 was tested for the ability to disrupt rosettes. This clone has a minimal effect on rosette state at 260 nM. An interesting fact about this clone is that the MFold prediction done on the 50 nt random region has no secondary structure whereas clones b02, d12 and e05 shows complex secondary structures. The aptamers tested in this study, were 90 nt with an approximate weight of 31 kDa. The fixed flanking regions of 2×20 nt for T7 RNA transcription and primer binding are included in the structures. These are not believed to be important for binding and therefore the active aptamers isolated in this study could be truncated to 40-50 nt or even less after further work has been done to elucidate the regions of the aptamers that are important for binding. The given structures of the aptamers are only theoretical and RNA fingerprinting must be performed to verify the secondary structure of the given RNA. To summarize, the described results prove that DBL1 specific aptamers have the potential to locate DBL1 on the surface of infected erythrocytes for IFA imaging. More importantly the aptamers could be used as a novel anti-rosetting drug. The next step would be to test the aptamers for rosette disruption and sequestration of parasites in an animal model such as rat to see if the aptamers are active in vivo. Since the field of aptamers as therapeutic drugs is expanding a lot of knowledge on how to increase stability and activity of aptamers in vivo has been obtained. This greatly facilities the success in any future work conducted on aptamers in an in vivo situation. Finally it must be noted that the experimental approach might have a much broader application spectrum, especially in the case of extracellular pathogens where drug delivery through membranes is not required.

Culturing of *Plasmodium falciparum*.

Bloodstage parasites of *P. falciparum* strain FCR3S1.2 was cultivated according to standard methods with 10% $AB^+Rh^+$ serum added to buffered medium (RPMI supplemented with Hepes, gentamycin and sodium bicarbonate).

Protein Expression in *E. coli*.

Recombinant DBL1α$^{His}$ from FCR3S1.2 was expressed as follows, SG13009 (pREP4) cells from Qiagen harboring plasmids pQE-TriSystem His.Strep 2 (DBL1α$^{His}$), or pQE-60 (DBL1α$^{His}$) were grown in LB-medium containing ampicillin (100 μg/mL) and kanamycin (30 μg/mL) at either 22° C. or 37° C. At $OD_{600}$=0.8 cells were induced with 0.1 mM IPTG for 3 h; 1 liter cell suspension was harvested (4° C., 25 min, 3000 g) and resuspended in 25 mL lysis buffer (50 mM $NaH_2PO_4$/NaOH pH 7.4, 300 mM NaCl, 1 mM PMSF (Sigma) 0.05% Triton x-100, 10 mM imidazole). Cells incubated with Lysozyme on ice for 30 min, and sonicated. Insoluble cell debris was removed by centrifugation (4° C. 30 min, 18.000 g). The supernatant was DNase treated and incubated with 1 mL NI-NTA agarose beads (Qiagen) for 2 h at 4° C. with gentle agitation. Beads were pelleted at 100× g for 3 min. and washed 3 times with 15 mL wash buffer (50 mM $NaH_2PO_4$/NaOH pH 7.4, 300 mM NaCl, 0.05% Triton x-100, 30 mM Imidazole). Bound protein was eluted with 400 mM imidazole (Sigma), 50 mM $NaH_2PO_4$, 300 mM NaCl which was subsequently removed by dialysis against PBS buffer with 0.05% Triton X-100 for 18 h at 4° C. Protein purity was estimated by running samples on 10% SDS-PAGE and finally protein concentration was determined (Bradford 1976). Alternatively, His-tagged DBL1α was purified on FPLC. *E. coli* extracted soluble fraction was loaded onto Ni-column on FPLC (AmershamBiosciences) with a flow speed of 0.5 mL/min. Bound protein was washed with 5-70 mM Imidazole gradient (60 mL at 1 mL/min). Protein was eluted with 400 mM imidazole and analysed as previously described. All chemicals were obtained from Sigma.

In Vitro Selection—SELEX.

The DNA library mentioned above was generated using

```
oligonucleotide B
                                            (SEQ. ID. NO. 19)
(5'-CGACTGCAGAGCTTGCTACG(N)50GGTACCGAGCTCGAATTCCC-
3')
```
and
```
oligonucleotide A
                                            (SEQ. ID. NO. 20)
(5'-GCGTAATACGACTCACTATAGGGAATTCGAGCTCGGTACC-3')
```

(sequence for T7 promotor underlined). Oligonucleotides were synthesized and purchased from IBA, Germany. Oligonucleotide B contains a central sequence of 50 randomised nucleotides flanked by constant regions for annealing to oligonucleotide A and a primer site for reverse transcription. Double stranded DNA Library was created by annealing 3 μM of oligonucleotide A and oligonucleotide B (95° C. for 5 min and cool 15 min at 25° C.), subsequently adding Klenow fragment (Fermentas) in Klenow buffer (Fermentas) at 37° C. for 2 h. dsDNA is purified by microcon Ym-30 column (Millipore) and eluted in 30 μl RNAse free water. 2'F-modified library was created by T7 RNA transcription of 40 μg template using T7 polymerase (Epicentre) in supplied transcription buffer adding DTT (Epicentre) to 10 mM and ATP, GTP, 2'F-dCTP, 2'F-dUTP (Epicentre) to 1.25 mM. RNA was labelled by adding 0.37 MBq [α-$^{32}$P]-ATP (Amersham Biosciences) in 20 μl reaction volume. Reaction ran at 37° C. for 5 h and DNA/RNA was precipitated using 0.2 M NaOAc, 70% EtOH. Sample ran on 10% 8 M UREA PAGE and radioactive RNA was cut out from gel and purified by crushing and soaking with 1 M NaOAc (pH=4.7) over night. After centrifugation with glass wool RNA was precipitated (70% EtOH and Glycogen to 0.05%).

The first selection cycle was performed with 30 µg (1 nmol) radioactive labelled 2'F-RNA and a minimum of 60 µg (1, 3 nmol) purified DBL1α. Subsequent cycles were performed with approx. 300 pmol RNA and varying amounts of protein from 20 µg to 60 µg. His-tagged DBL1α was bound to Ni-NTA agarose (Qiagen) in cycles 1-4 and 7-8 and to Ni-NTA Magnetic beads (Qiagen) cycles 5 and 6. The concentration of protein and RNA was 800 nM to 1.2 µM with varying ratios between RNA/Protein (1:1-4). This concentration range is chosen as other molecules which are suppose to work in a similar manner e.g. heparin sulphate gives the same values in a 10fold higher concentration. A pre-selection on 100 µl Ni-NTA agarose was performed in every cycle before incubation with DBL1α to avoid enrichment of matrix binders. Incubation of RNA with DBL1α was performed at 37° C. with gentle agitation for 60 min. in starting cycles and 20 min. in later cycles. Beads were washed with 2×500 µl PBSM and RNA/Protein eluted with 7M UREA, 400 mM imidazole, 50 mM $NaH_2PO_4$ (pH=7.4). RNA was extracted using phenol/chloroform and precipitated with NaOAc/EtOH. The RNA recovery in each cycle was determined by measuring the radioactivity of all collected fractions during the experiment using a scintillator.

RNA concentration was estimated using Nanodrop and ssDNA was generated by adding primer B (5'-CGACTGCA-GAGCTTGCTACG-3') in excess and 20 units of M-MuLV-RT (Fermentas) in supplied buffer and 1 mM dNTP. Reaction ran at 37° C. for 2 h. 2'F-RNA was partly degraded by addition of 0.1 M NaOH at 37° C. for 30 min. ssDNA was purified using Ym-30 microcon column and concentration was determined using Nanodrop. To the ssDNA, oligonucleotide A was added in a 1:1 ratio. After annealing the two oligonucleotides, full length dsDNA was created by Klenow fill out. dsDNA was amplified by PCR using Taq DNA polymerase (Fermentas) with a maximum of 14 cycles using primer A (5'-GCG-TAATACGACTCACTATAG-3') and primer B. PCR product was pooled and purified and used as template for next SELEX cycle.

Cloning and Sequencing of RNA Aptamer.

PCR amplified dsDNA from pool 8 was cloned into TOPO vector pCR®4 or pCR®2.1 from Invitrogen and transformed into *E.coli* strain Top10 (Invitrogen). Cells were spread on LB-agar with 100 µg/mL ampicillin and 30 µg/mL 5-bromo-4-chloro-3-indolyl-b-D-galacto-pyranoside (X-Gal). White colonies were isolated and insert confirmed by colony-PCR using M13-reverse and -forward primer. Positive clones were streaked onto a 96 well plate and sent to AGOWA (Germany) for sequencing using M13 primer. 70 Sequences were aligned and screened for conserved motifs using the MEME/MAST system motif discovery search version 3.5.4. (http://meme.s-dsc.edu/meme).

Transcription of Individual Aptamers and Their Binding to DBL1α$^{His}$.

Individual *E. coli* clones were picked from LB-amp plate and grown in 5 mL LB-amp (100 µg/mL) at 37° C. over night. Plasmid was isolated using miniprep kit (Sigma) on 3 mL cell culture. Plasmid was eluted in 100 µl water. Transcription template was generated using primer A and primer B for PCR. Prior PCR amplification vector was cleaved with Not I to avoid the production of incorrect PCR products. PCR product was purified by centrifugation on Ym-30 column (Millipore). T7 transcription of 500 ng dsDNA template was done in 20 µl with 1.25 mM 2'F-dNTP (Epicentre) and NTP (Fermentas), 10 mM DTT (Epicentre), 0.37 Mbq [α-$^{32}$P]-ATP (Amersham Bioscience) ran at 37° C. for 3 h. Template was digested using 1 unit of DNAse at 37° C. for 15 min. RNA was purified using MICROCON®. RNA concentration was determined using NanoDrop.

Electrophoretic Mobility Shift Assay.

25-30 ng internal $^{32}$P-[α-ATP] labelled RNA was incubated in a volume of 18 µl with 4-5 µl (~300 ng) of fresh eluted DBL1α$^{His}$ and 3 µg yeast RNA was added in PBSM. Sample without DBL1α$^{His}$ was incubated in the presence of 10 µg BSA and 4-5 µl 400 mM imidazole elution buffer was added to the BSA sample so the control was identical to the sample incubated with DBL1α. Samples were incubated at 37° C. for 10 min and 6× loading buffer were added (Maniatis). 10 µl of sample was loaded on a 1 mm thick 10% PAA gel and run at 80 V for 30 min and then run at 200 V until lower migration dye (Bromophenol Blue) had run out from gel. Phosphor image plate (Brand) was exposed overnight and plate was analysed on a Storm phosphor imager.

Fluorescein Labelling of Aptamer.

The aptamer RNA was cotranscriptionally labelled with fluorescein. The transcription mix contained NTP labelling mixture (10 mM ATP, 10 mM CTP, 10 mM GTP, 6.5 mM UTP and 3.5 mM fluorescein-12-UTP, pH 7.5) (Roche Applied Science), 5× T7 transcription buffer, 2 µl T7 polymerase (50 U/µl, Fermentas), sterile RNase free d$H_2O$ (Fluka), and 200 ng template DNA per 20 µl reaction. The reaction was performed at 37° C. for 2 h. The transcription product was DNase treated (New England BioLabs Inc); EtOH/NaOAc precipitated twice and purified using MICROCON® (MILLIPORE).

Live Cell Assay, Fluorescence Microscopy and Imagin.

*P. falciparum* parasites (strain FCR3S1.2) were cultivated to trophozoite stage and adjusted to a parasitemia of 4-5%. The parasitized erythrocytes (PE) were washed twice with sterile PBS, the supernatant was discarded and the pellet was resuspended in approximately 200 µL sterile PBS. For the live cell assay, monolayers were prepared on adhesive slides (Marienfeld Glassware) according to the manufacturer's protocol. Negatively charged cells are bound to these slides based on electrostatic adhesion without additional fixation steps allowing the investigation of live late-stage parasitized erythrocytes. The cells were washed with sterile PBS and 500 ng of the RNA sample dissolved in 20 µL PBS 1% BSA was added and allowed to incubate for 30 minutes. As negative control in this experiment, aptamer RNA from pool 0 was used. Unbound RNA was removed by washing with sterile PBS and Vectasheild® Mounting medium with DAPI (4.6-diamidino-2-phenylindole) (Vector) was added. All incubations were carried out at room temperature in a humid chamber. Slides were analyzed with a 100× oil immersion lens in a Nikon Optiphot 2 UV microscope.

Rosetting Disruption Assay.

RNA samples for the disruption assay were eluted with water and 1 mM $MgCl_2$. *Plasmodium falciparum* strain FCR3S1.2 was cultured to a parasitimia of 4-5% in 5% hematocrit using candle jar technique (ref. Vogt). The cell culture was mixed with the RNA samples to a finale volume of 100 µl in concentrations from 130 nM to 750 nM. Negative controls were performed either with the addition of water/$MgCl_2$ or unselected RNA generated with T7 transcription from unselected pool 0 dsDNA. Parasites were incubated from 1 to 2½ hours at room temperature with gentle agitation. Culture was mixed with RPMI/Acridine Orange and analysed using microscope for rosetting status. Counting was done blind and unbiased and a minimum of 400 parasites were counted for each sample. Rosetting parasites were defined as infected erythrocytes with more than 2 attached uninfected erythrocytes. Upon auto-agglutination each individual parasite in a cluster was counted as a rosetting parasite. Rosetting rate was calculated as (rosetting parasites/(rosetting parasites+non-rosetting parasites)×100.

We have been able to show the rosette disrupting capacity of these SELEX-aptamers at concentrations of 33 nM and with 100% disruption at 387 nM. Furthermore, that they have a half time in serum of 20 h.

Aptamer binding to GST-DBL1α. To confirm that the interaction of the new aptamers with the protein was specific an additional experiment was designed. Non-labeled RNA was to compete with radioactive 5' labeled RNA for binding to a GST-DBL1α fusion protein. The recovery of labeled RNA decreases 40% with the addition of 30 fold molar excess of non-labeled RNA. The two negative controls in the experiment, unselected RNA (pool 0) and e02, gave a 85-90% lower recovery if compared to b02, d12, e05.

To further confirm that the observed decrease is specific, radioactive labeled d12 was incubated in the presence of 30 fold molar excess of e02 and pool 0. No decrease was observed with the addition of RNA from these two pools. Furthermore, an additional decrease from 40% to 60% of labeled RNA was demonstrated when 45 fold molar excess of the non-labeled d12 RNA was added.

Aptamer binding to the surface of infected erythrocytes. As the selected aptamers were binding to the recombinant DBL1α domain the next step was to verify if they could be associated to the surface of the infected erythrocyte. Two of these aptamers was compared to unselected RNA from pool 0 and the non-binding aptamer e02. Equal molar amounts of RNA were end-labeled with $^{32}P$ and incubated with 5% parasitemia culture of FCR3S1.2. The results demonstrate that the selected RNA is retained 4 fold higher than RNA from unselected pool or the non-binding aptamer e02.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those skilled in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatine capsule), the active drug component can be combined with an oral, non-toxic pharmaceutically acceptable inert carrier such as ethanol, glycerol, water and the like. Moreover, when desired or necessary, suitable binders, lubricants, disintegrating agents and colouring agents can also be incorporated into the mixture. Suitable binders include starch, magnesium aluminium silicate, starch paste, gelatine, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and typically contain about 0.1 to 75%, preferably about 1 to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Furthermore, preferred compounds for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines, hi some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds of the invention may also be delivered to the tissue through systemic blood and fluid to the tissues and so is administered by parenteral systemic injection, by intravenous, intramuscular or intrascleral routes of delivery. Administration via injection of pharmaceutical compositions of the invention may be useful as a supplement to systemic administration of a therapeutic for the treatment of malaria and/or systemic diseases with such manifestations.

Compounds of the present invention may also be administered to the tissue in depot or sustained release gel or polymer formulation by surgical implantation of a biodegradable microsize polymer system, e.g., microdevice, microparticle, or sponge, or other slow release transscleral devices, implanted during the treatment of a disease, or by a deliver device, e.g. polymer sustained delivery device. Compounds of the invention may also be administered to the tissue topically. e.g., in drop form loaded with the compound of the invention, or by iontophoresis using electric current to drive drug from the surface to the tissue.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician can readily determine and prescribe the effective amount of the drug required to prevent, counter or arrest the progress of the condition.

Oral dosages of the aptamer compositions of the present invention, when used for the indicated effects, will range between about 0.05 to 7500 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Compounds of the present invention may be administered in a single daily dose, or the total daily dosage may be administered in divided doses of two, three or four times daily.

Infused dosages, intranasal dosages and transdermal dosages of the aptamer compositions of the present invention will range between 0.05 to 7500 mg/day. Subcutaneous, intravenous and intraperineal dosages of the aptamer compositions of the present invention will range between 0.05 to 3800 mg/day.

Cerebral dosages of the aptamer compositions of the present invention will range between 0.001 to 10 mg administered, e.g. by injection, from once a week up to once every three months or by sustained release device or formulation.

Effective plasma levels of the aptamer compounds of the present invention range from 0.002 mg/mL to 50 mg/mL. Effective cerebral levels of the aptamer compounds of the invention can range from 20 nM to 250 µM. A concentration of 33 nM is enough to provide a disruption capacity, while 380 nM will provide a 100% disruption when it comes to aptamers SEQ. ID. NOs 6 to 9 and corresponding fluorinated ones SEQ. ID. NOs 10 to 12.

FIGURE LEGENDS

FIG. 1. Ni-NTA agarose purification of His-tagged DBL1α expressed in *E. coli*. Cells were induced with 100 µM IPTG at $OD_{600}$=1.2 and grown for three hours. Cells lysed with sonication in 10 mM imidazole and 0.1% Triton X-100. Ni-NTA agarose beads were washed with 20 mM to 90 mM imidazole and bound protein was eluted in phosphate buffer with 400 mM imidazole.

Figure 2:
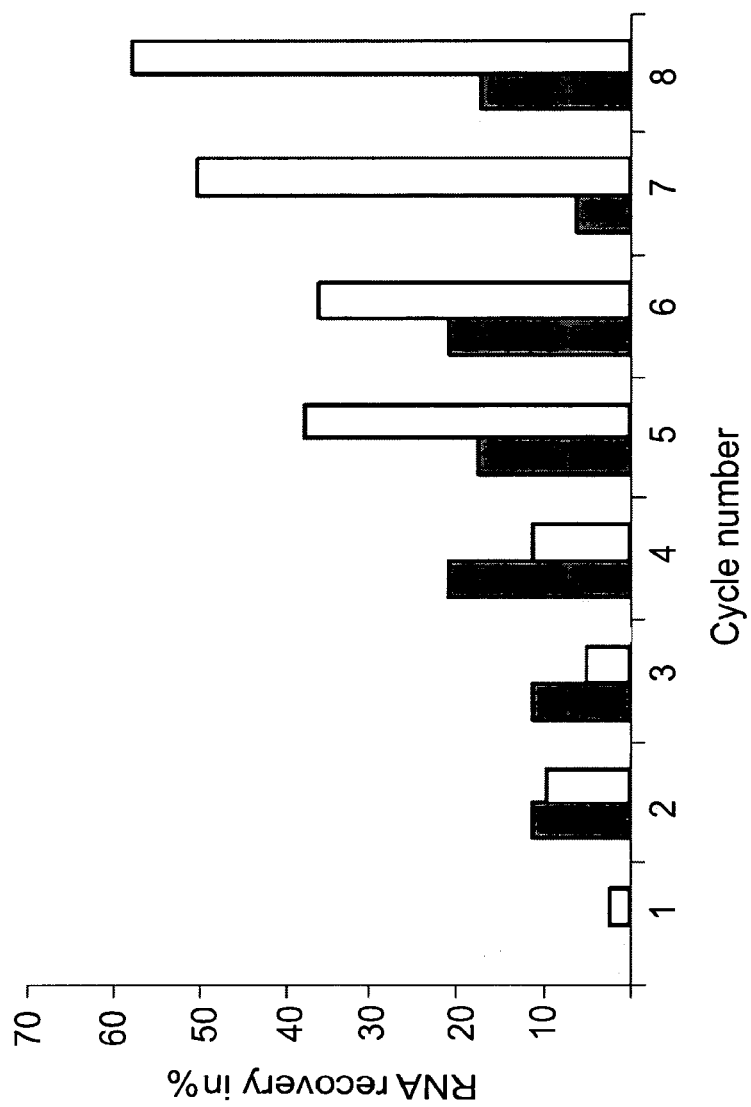

FIG. 2. In vitro selection using random RNA library of sequences with 2'-F substitution on UTP and CTP on purified DBL1α bound to either Ni-NTA agarose or Ni-NTA magnetic beads. Selection was done in PBS buffer containing 1 mM $MgCl_2$ with approximately 1 µM protein and RNA in a 2:1 ration, at 37° C. and with 30 minutes incubation. Bound RNA was phenol-chloroform extracted and converted to dsDNA by reverse transcription and Klenow fill-in reaction, followed by PCR amplification.

Figure 3:
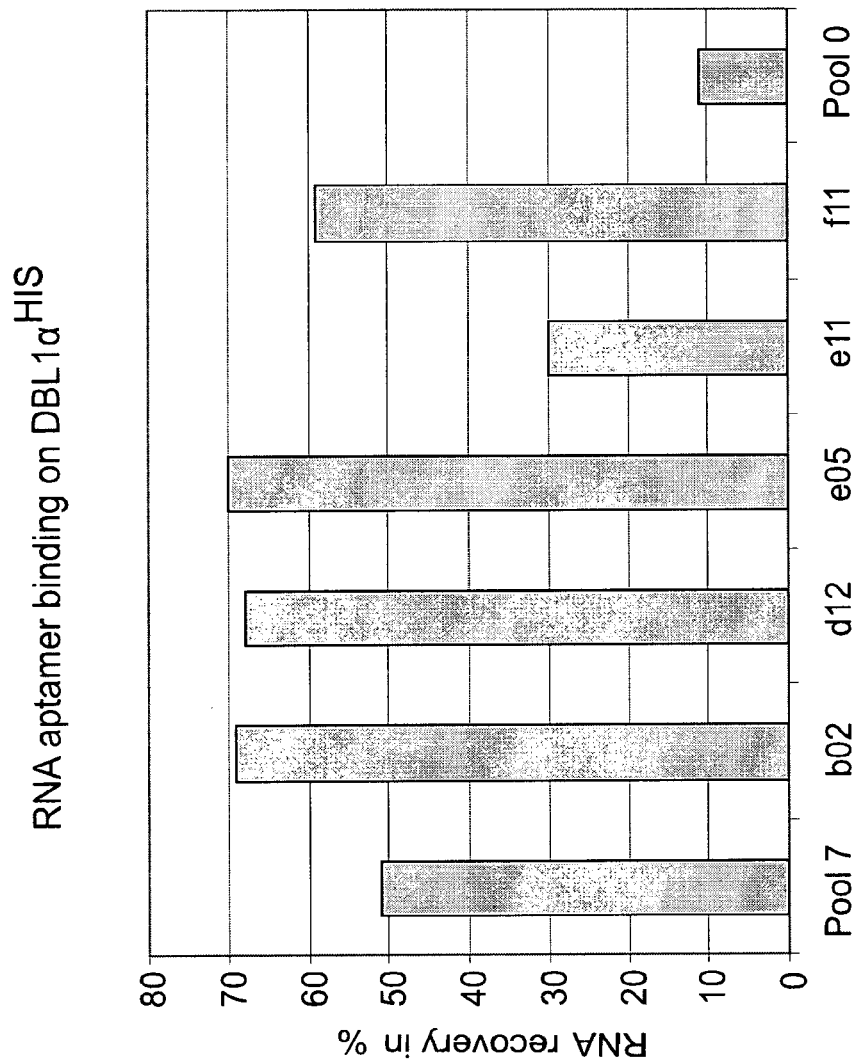

FIG. 3. The binding of radioactive labelled RNA on *E.coli* purified DBL1α$^{His}$. 40 nM $^{32}$P-labeled 2'F-RNA was incubated 45 min at 37° C. with agitation with 350-400 nM DBL1α$^{His}$ in 800 µl PBSM supplied with 600 µg yeast RNA. Beads were washed with 2×1 mL PBS and bound RNA/DBL1α$^{His}$ was eluted with 500 mM imidazole. All fractions collected and RNA recovery was estimated by scintillation count.

FIG. 4. Mobility shift assay of selected clones incubated in the presence of DBL1α$^{His}$. 25-30 ng internal $^{32}$P-[αATP] labelled RNA was incubated 10 min. with ~300 ng DBL1α$^{His}$ and run on 10% TBE-buffered PAA gel (+). In the negative control (−). 25-30 ng internal $^{32}$P-[αATP] was incubated with 10 µg BSA and loaded on gel.

Figure 5:
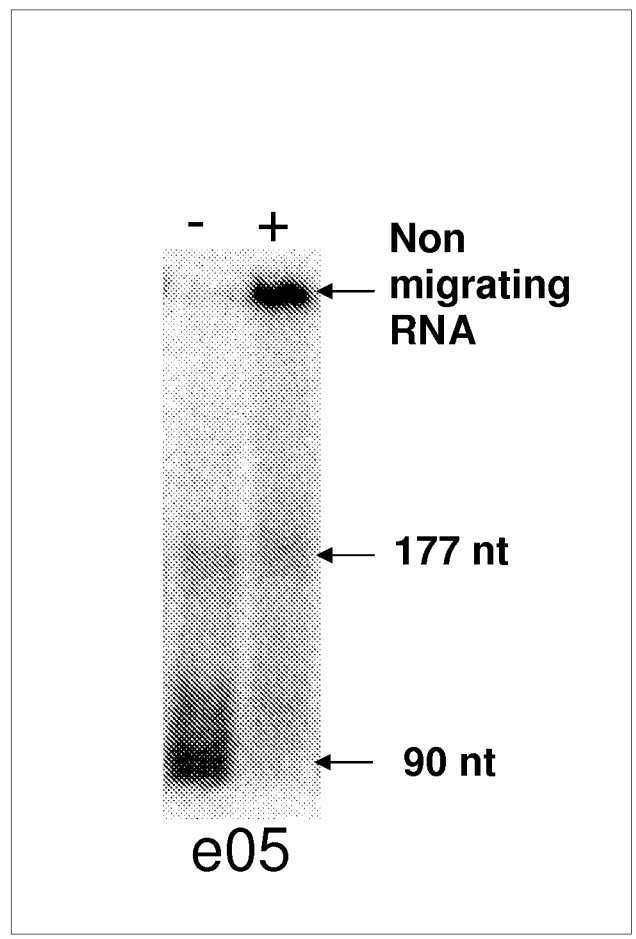

FIG. 5. Mobility shift assay of selected clone e05. ~30 ng internal $^{32}$P-[αATP] labelled RNA was incubated with ~300-400 ng DBL1α$^{His}$ for 10 min. and loaded on 10% TBE-buffered PAA gel (+) together with negative control (−) incubated in the presence of 10 µg BSA.

Figure 6:
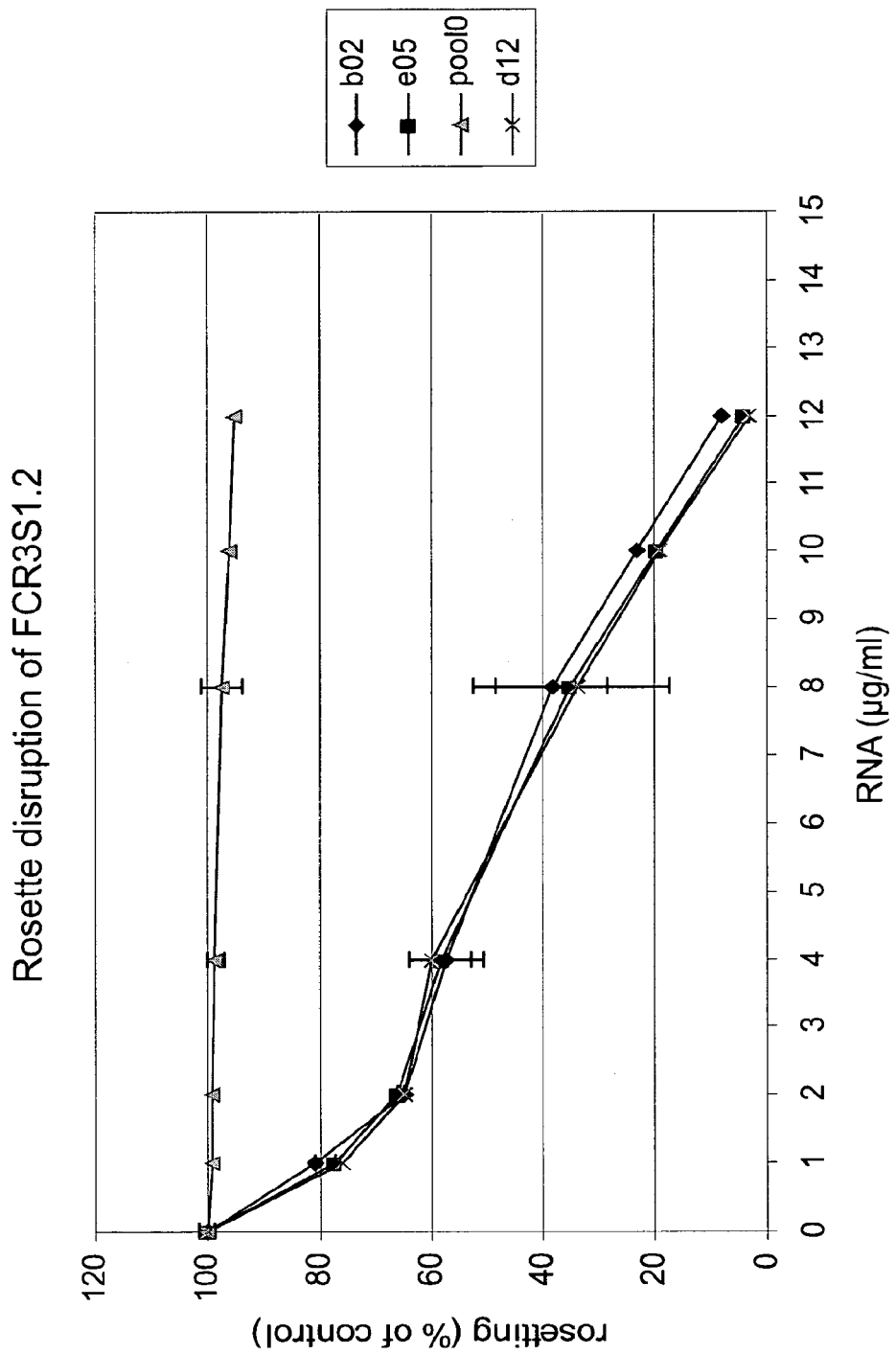

FIG. 6. Analysis of live cell assay in fluorescence microscopy. (a) Fluorescein labelled RNA from pool 8 associated to DAPI stained parasitized erythrocytes. The same association of fluorescein labelled RNA is not noticeable towards unparasitized erythrocytes which are seen as black patches. (b) A cut out from the previous picture. (c) Although fluorescein labelled RNA from pool 0 to some extent is associated to DAPI stained parasitized erythrocytes, it is not nearly as distinct as the association between parasite and pool 8 RNA.

Figure 7:
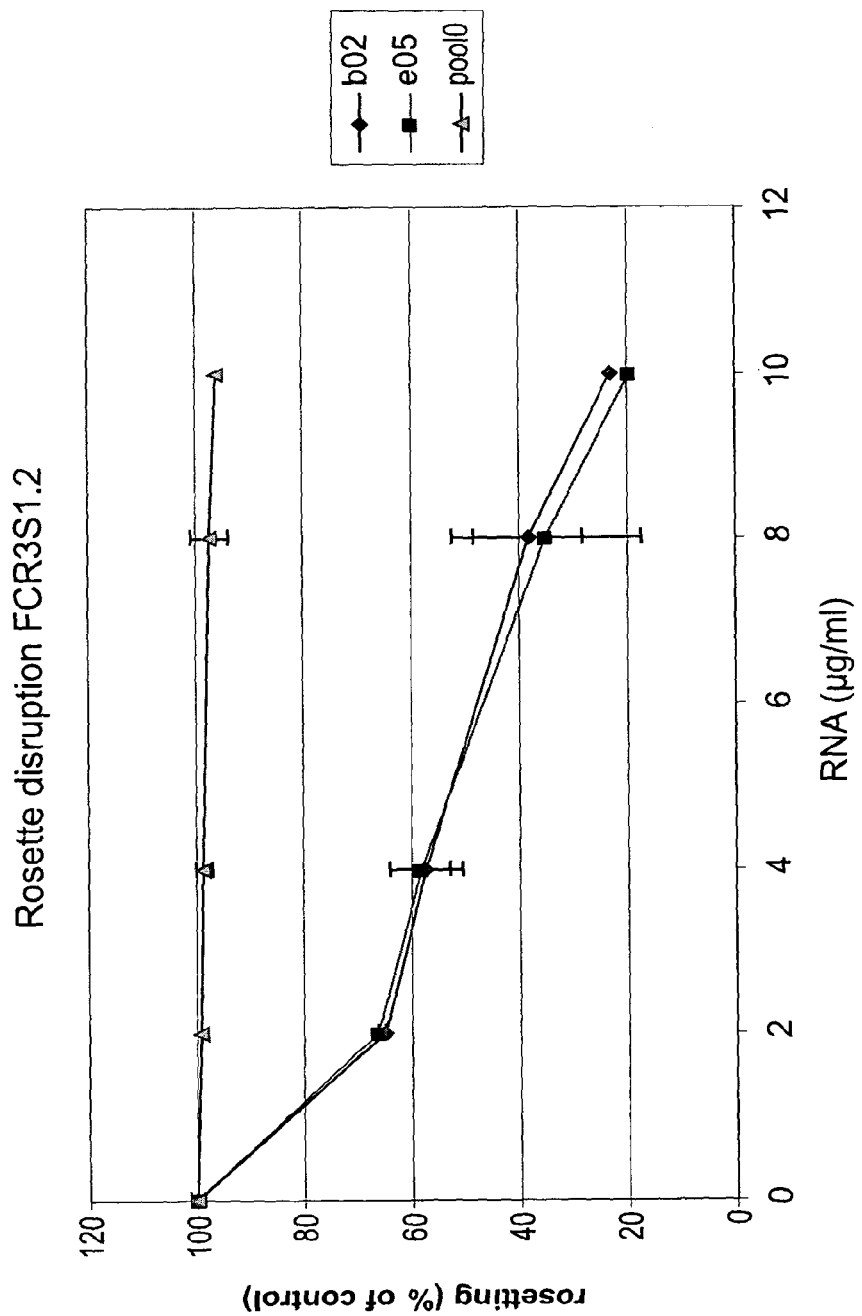
Figure 8:
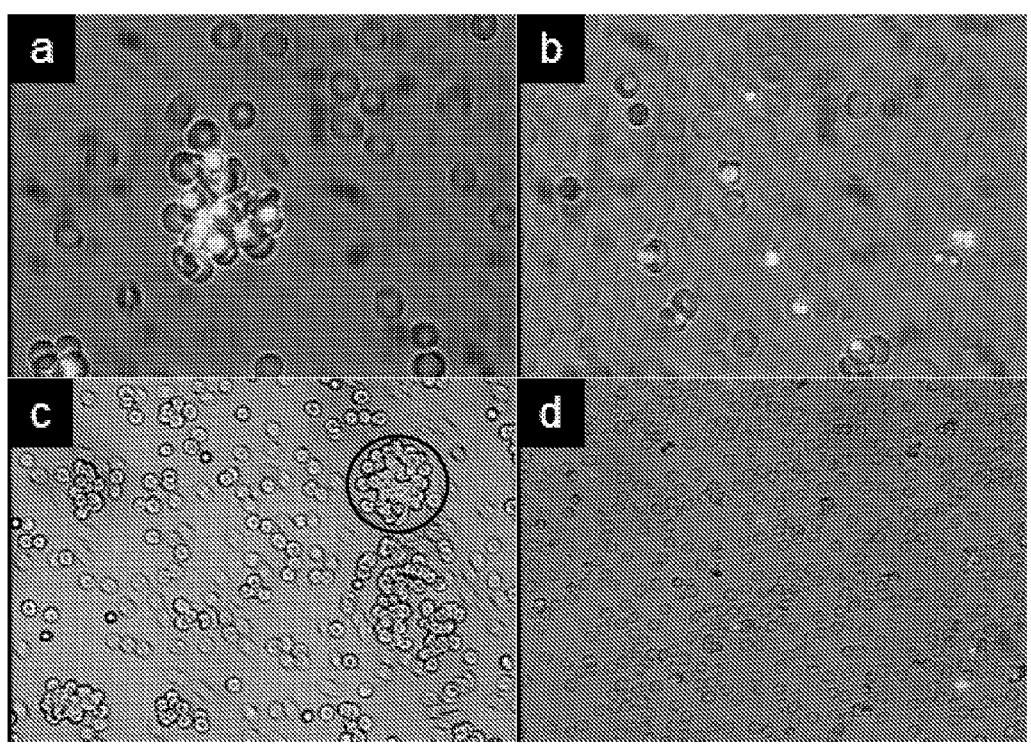

FIG. 7. Preliminary figure of the rosetting disruption effect of clone e05 and b02 compared to unselected pool 0 RNA. In the finale figure display concentration of aptamer on x-axis with 1 or 2-4-8-12 µg/mL and include e02 as a aptamer with no apparent effect.

FIG. 8. Shows status of control and of disrupted rosettes. Rosette disruption of FCR3S1.2. Fluorescence microscopy of cells stained with acridine orange with 40× or 20× magnification. Images (a) and (c) are control cells which have incubated with 2 µl water in 98 µl cells for one hour. (b) and (d) are cells treated with 2 µl (800 ng) 2'F-RNA from SELEX clone d12. In image (c) a giant rosette is enclosed in circle.

The invention claimed is:

1. An aptamer comprising:

(SEQ. ID. NO. 6)
GUGACCACGCGGAUAAAUGAAUCAAAAACAACAACCAGGGCCGUUCGACU

ACGCUAAUUAUCCCG.

2. An aptamer which is fluorinated aptamer of SEQ ID NO: 6 having sequence:

(SEQ. ID. NO. 12)
GU$^F$GAC$^F$C$^F$AC$^F$GC$^F$GGAU$^F$AAAU$^F$GAAU$^F$C$^F$AAAAAC$^F$AAC$^F$AAC$^F$C$^F$A

GGGC$^F$C$^F$GU$^F$U$^F$C$^F$GAC$^F$U$^F$AC$^F$GC$^F$U$^F$AAU$^F$U$^F$AU$^F$C$^F$C$^F$C$^F$G.

3. The aptamer of claim 1, wherein the aptamer consists of SEQ ID NO: 6.

4. The aptamer of claim 2, wherein the aptamer consists of SEQ ID NO: 12.

* * * * *

```
                         SEQUENCE LISTING

<160> NUMBER OF SEQ ID NOS: 24

<210> SEQ ID NO 1
<211> LENGTH: 50
<212> TYPE: RNA
<213> ORGANISM: Artificial Sequence
<220> FEATURE:
<223> OTHER INFORMATION: Aptamer against a region of a protein of
      Plasmodium falciparum

<400> SEQUENCE: 1
ugccaaccuu cgaugcaaga uaauacuuuu gaugguguag ucguauuguu            50

<210> SEQ ID NO 2
<211> LENGTH: 52
<212> TYPE: RNA
<213> ORGANISM: Artificial Sequence
<220> FEATURE:
<223> OTHER INFORMATION: Aptamer against a region of a protein of
      Plasmodium falciparum

<400> SEQUENCE: 2
ucaugugcca guguuugaaa aaacgcguug auugcuggug uggugagcua gu         52

<210> SEQ ID NO 3
<211> LENGTH: 53
<212> TYPE: RNA
<213> ORGANISM: Artificial Sequence
<220> FEATURE:
<223> OTHER INFORMATION: Aptamer against a region of a protein of
      Plasmodium falciparum

<400> SEQUENCE: 3
cuucgaacgg cccugguugu ugguuuuaau ucauuuaucc gcguggucac ggu        53

<210> SEQ ID NO 4
<211> LENGTH: 50
<212> TYPE: RNA
<213> ORGANISM: Artificial Sequence
<220> FEATURE:
<223> OTHER INFORMATION: Aptamer against a region of a protein of
      Plasmodium falciparum

<400> SEQUENCE: 4
uagcucacca caccagcaau caacgcguuu uuucaaacac uggcacauga            50

<210> SEQ ID NO 5
<211> LENGTH: 50
<212> TYPE: RNA
<213> ORGANISM: Artificial Sequence
<220> FEATURE:
<223> OTHER INFORMATION: Aptamer against a region of a protein of
      Plasmodium falciparum
```

```
<400> SEQUENCE: 5
aacaauacga cuacaccauc aaaaguauua ucuugcaucg aagguuggca          50

<210> SEQ ID NO 6
<211> LENGTH: 65
<212> TYPE: RNA
<213> ORGANISM: Artificial Sequence
<220> FEATURE:
<223> OTHER INFORMATION: Aptamer against a region of a protein of
      Plasmodium falciparum

<400> SEQUENCE: 6
gugaccacgc ggauaaauga aucaaaaaca acaaccaggg ccguucgacu acgcuaauua          60
ucccg                                                                      65

<210> SEQ ID NO 7
<211> LENGTH: 50
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: fluroinated, Aptamer against protein region of
      Plasmodium falciparum
<220> FEATURE:
<221> NAME/KEY: misc_feature
<222> LOCATION: (3)..(3)
<223> OTHER INFORMATION: fluroinated, Aptamer against protein region of
      Plasmodium falciparum
<220> FEATURE:
<221> NAME/KEY: misc_feature
<222> LOCATION: (4)..(4)
<223> OTHER INFORMATION: fluroinated, Aptamer against protein region of
      Plasmodium falciparum
<220> FEATURE:
<221> NAME/KEY: misc_feature
<222> LOCATION: (7)..(7)
<223> OTHER INFORMATION: fluroinated, Aptamer against protein region of
      Plasmodium falciparum
<220> FEATURE:
<221> NAME/KEY: misc_feature
<222> LOCATION: (8)..(8)
<223> OTHER INFORMATION: fluroinated, Aptamer against protein region of
      Plasmodium falciparum
<220> FEATURE:
<221> NAME/KEY: misc_feature
<222> LOCATION: (9)..(9)
<223> OTHER INFORMATION: fluroinated, Aptamer against protein region of
      Plasmodium falciparum
<220> FEATURE:
<221> NAME/KEY: misc_feature
<222> LOCATION: (10)..(10)
<223> OTHER INFORMATION: fluroinated, Aptamer against protein region of
      Plasmodium falciparum
<220> FEATURE:
<221> NAME/KEY: misc_feature
<222> LOCATION: (11)..(11)
<223> OTHER INFORMATION: fluroinated, Aptamer against protein region of
      Plasmodium falciparum
<220> FEATURE:
<221> NAME/KEY: misc_feature
<222> LOCATION: (14)..(14)
<223> OTHER INFORMATION: fluroinated, Aptamer against protein region of
      Plasmodium falciparum
<220> FEATURE:
<221> NAME/KEY: misc_feature
<222> LOCATION: (16)..(16)
<223> OTHER INFORMATION: fluroinated, Aptamer against protein region of
      Plasmodium falciparum
<220> FEATURE:
<221> NAME/KEY: misc_feature
<222> LOCATION: (21)..(21)
<223> OTHER INFORMATION: fluroinated, Aptamer against protein region of
      Plasmodium falciparum
```

```
-continued

<220> FEATURE:
<221> NAME/KEY: misc_feature
<222> LOCATION: (24)..(24)
<223> OTHER INFORMATION: fluroinated, Aptamer against protein region of
      Plasmodium falciparum
<220> FEATURE:
<221> NAME/KEY: misc_feature
<222> LOCATION: (26)..(26)
<223> OTHER INFORMATION: fluroinated, Aptamer against protein region of
      Plasmodium falciparum
<220> FEATURE:
<221> NAME/KEY: misc_feature
<222> LOCATION: (27)..(27)
<223> OTHER INFORMATION: fluroinated, Aptamer against protein region of
      Plasmodium falciparum
<220> FEATURE:
<221> NAME/KEY: misc_feature
<222> LOCATION: (28)..(28)
<223> OTHER INFORMATION: fluroinated, Aptamer against protein region of
      Plasmodium falciparum
<220> FEATURE:
<221> NAME/KEY: misc_feature
<222> LOCATION: (29)..(29)
<223> OTHER INFORMATION: fluroinated, Aptamer against protein region of
      Plasmodium falciparum
<220> FEATURE:
<221> NAME/KEY: misc_feature
<222> LOCATION: (30)..(30)
<223> OTHER INFORMATION: fluroinated, Aptamer against protein region of
      Plasmodium falciparum
<220> FEATURE:
<221> NAME/KEY: misc_feature
<222> LOCATION: (33)..(33)
<223> OTHER INFORMATION: fluroinated, Aptamer against protein region of
      Plasmodium falciparum
<220> FEATURE:
<221> NAME/KEY: misc_feature
<222> LOCATION: (36)..(36)
<223> OTH -continued
<220> FEATURE:
<221> NAME/KEY: misc_feature
<222> LOCATION: (50)..(50)
<223> OTHER INFORMATION: fluroinated, Aptamer against protein region of
      Plasmodium falciparum

<400> SEQUENCE: 7
ugccaaccuu cgaugcaaga uaauacuuuu gauggugu ag ucguauuguu 50

<210> SEQ ID NO 8
<211> LENGTH: 52
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: fluroinated, Aptamer against protein region of
      Plasmodium falciparum
<220> FEATURE:
<221> NAME/KEY: misc_feature
<222> LOCATION: (2)..(2)
<223> OTHER INFORMATION: fluroinated, Aptamer against protein region of
      Plasmodium falciparum
<220> FEATURE:
<221> NAME/KEY: misc_feature
<222> LOCATION: (4)..(4)
<223> OTHER INFORMATION: fluroinated, Aptamer against protein region of
      Plasmodium falciparum
<220> FEATURE:
<221> NAME/KEY: misc_feature
<222> LOCATION: (6)..(6)
<223> OTHER INFORMATION: fluroinated, Aptamer against protein region of
      Plasmodium falciparum
<220> FEATURE:
<221> NAME/KEY: misc_feature
<222> LOCATION: (8)..(8)
<223> OTHER INFORMATION: fluroinated, Aptamer against protein region of
      Plasmodium falciparum
<220> FEATURE:
<221> NAME/KEY: misc_feature
<222> LOCATION: (9)..(9)
<223> OTHER INFORMATION: fluroinated, Aptamer against protein region of
      Plasmodium falciparum
<220> FEATURE:
<221> NAME/KEY: misc_feature
<222> LOCATION: (12)..(12)
<223> OTHER INFORMATION: fluroinated, Aptamer against protein region of
      Plasmodium falciparum
<220> FEATURE:
<221> NAME/KEY: misc_feature
<222> LOCATION: (14)..(14)
<223> OTHER INFORMATION: fluroinated, Aptamer against protein region of
      Plasmodium falciparum
<220> FEATURE:
<221> NAME/KEY: misc_feature
<222> LOCATION: (15)..(15)
<223> OTHER INFORMATION: fluroinated, Aptamer against protein region of
      Plasmodium falciparum
<220> FEATURE:
<221> NAME/KEY: misc_feature
<222> LOCATION: (16)..(16)
<223> OTHER INFORMATION: fluroinated, Aptamer against protein region of
      Plasmodium falciparum
<220> FEATURE:
<221> NAME/KEY: misc_feature
<222> LOCATION: (24)..(24)
<223> OTHER INFORMATION: fluroinated, Aptamer against protein region of
      Plasmodium falciparum
<220> FEATURE:
<221> NAME/KEY: misc_feature
<222> LOCATION: (26)..(26)
<223> OTHER INFORMATION: fluroinated, Aptamer against protein region of
      Plasmodium falciparum

```
<220> FEATURE:
<221> NAME/KEY: misc_feature
<222> LOCATION: (28)..(28)
<223> OTHER INFORMATION: fluroinated, Aptamer against protein region of
      Plasmodium falciparum
<220> FEATURE:
<221> NAME/KEY: misc_feature
<222> LOCATION: (29)..(29)
<223> OTHER INFORMATION: fluroinated, Aptamer against protein region of
      Plasmodium falciparum
<220> FEATURE:
<221> NAME/KEY: misc_feature
<222> LOCATION: (32)..(32)
<223> OTHER INFORMATION: fluroinated, Aptamer against protein region of
      Plasmodium falciparum
<220> FEATURE:
<221> NAME/KEY: misc_feature
<222> LOCATION: (33)..(33)
<223> OTHER INFORMATION: fluroinated, Aptamer against protein region of
      Plasmodium falciparum
<220> FEATURE:
<221> NAME/KEY: misc_feature
<222> LOCATION: (35)..(35)
<223> OTHER INFORMATION: fluroinated, Aptamer against protein region of
      Plasmodium falciparum
<220> FEATURE:
<221> NAME/KEY: misc_feature
<222> LOCATION: (36)..(36)
<223> OTHER INFORMATION: fluroinated, Aptamer against protein region of
      Plasmodium falciparum
<220> FEATURE:
<221> NAME/KEY: misc_feature
<222> LOCATION: (39)..(39)
<223> OTHER INFORMATION: fluroinated, Aptamer against protein region of
      Plasmodium falciparum
<220> FEATURE:
<221> NAME/KEY: misc_feature
<222> LOCATION: (41)..(41)
<223> OTHER INFORMATION: fluroinated, Aptamer against protein region of
      Plasmodium falciparum
<220> FEATURE:
<221> NAME/KEY: misc_feature
<222> LOCATION: (44)..(44)
<223> OTHER INFORMATION: fluroinated, Aptamer against protein region of
      Plasmodium falciparum
<220> FEATURE:
<221> NAME/KEY: misc_feature
<222> LOCATION: (48)..(48)
<223> OTHER INFORMATION: fluroinated, Aptamer against protein region of
      Plasmodium falciparum
<220> FEATURE:
<221> NAME/KEY: misc_feature
<222> LOCATION: (49)..(49)
<223> OTHER INFORMATION: fluroinated, Aptamer against protein region of
      Plasmodium falciparum
<220> FEATURE:
<221> NAME/KEY: misc_feature
<222> LOCATION: (52)..(52)
<223> OTHER INFORMATION: fluroinated, Aptamer against protein region of
      Plasmodium falciparum

<400> SEQUENCE: 8
ucaugugcca guguuugaaa aaacgcguug auugcuggug uggugagcua gu            52

<210> SEQ ID NO 9
<211> LENGTH: 53
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: fluroinated, Aptamer against protein region of
      Plasmodium falciparum
```

-continued

```
<220> FEATURE:
<221> NAME/KEY: misc_feature
<222> LOCATION: (2)..(2)
<223> OTHER INFORMATION: fluroinated, Aptamer against protein region of
      Plasmodium falciparum
<220> FEATURE:
<221> NAME/KEY: misc_feature
<222> LOCATION: (3)..(3)
<223> OTHER INFORMATION: fluroinated, Aptamer against protein region of
      Plasmodium falciparum
<220> FEATURE:
<221> NAME/KEY: misc_feature
<222> LOCATION: (4)..(4)
<223> OTHER INFORMATION: fluroinated, Aptamer against protein region of
      Plasmodium falciparum
<220> FEATURE:
<221> NAME/KEY: misc_feature
<222> LOCATION: (8)..(8)
<223> OTHER INFORMATION: fluroinated, Aptamer against protein region of
      Plasmodium falciparum
<220> FEATURE:
<221> NAME/KEY: misc_feature
<222> LOCATION: (11)..(11)
<223> OTHER INFORMATION: fluroinated, Aptamer against protein region of
      Plasmodium falciparum
<220> FEATURE:
<221> NAME/KEY: misc_feature
<222> LOCATION: (12)..(12)
<223> OTHER INFORMATION: fluroinated, Aptamer against protein region of
      Plasmodium falciparum
<220> FEATURE:
<221> NAME/KEY: misc_feature
<222> LOCATION: (13)..(13)
<223> OTHER INFORMATION: fluroinated, Aptamer against protein region of
      Plasmodium falciparum
<220> FEATURE:
<221> NAME/KEY: misc_feature
<222> LOCATION: (14)..(14)
<223> OTHER INFORMATION: fluroinated, Aptamer against protein region of
      Plasmodium falciparum
<220> FEATURE:
<221> NAME/KEY: misc_feature
<222> LOCATION: (17)..(17)
<223> OTHER INFORMATION: fluroinated, Aptamer against protein region of
      Plasmodium falciparum
<220> FEATURE:
<221> NAME/KEY: misc_feature
<222> LOCATION: (18)..(18)
<223> OTHER INFORMATION: fluroinated, Aptamer against protein region of
      Plasmodium falciparum
<220> FEATURE:
<221> NAME/KEY: misc_feature
<222> LOCATION: (20)..(20)
<223> OTHER INFORMATION: fluroinated, Aptamer against protein region of
      Plasmodium falciparum
<220> FEATURE:
<221> NAME/KEY: misc_feature
<222> LOCATION: (21)..(21)
<223> OTHER INFORMATION: fluroinated, Aptamer against protein region of
      Plasmodium falciparum
<220> FEATURE:
<221> NAME/KEY: misc_feature
<222> LOCATION: (24)..(24)
<223> OTHER INFORMATION: fluroinated, Aptamer against protein region of
      Plasmodium falciparum
<220> FEATURE:
<221> NAME/KEY: misc_feature
<222> LOCATION: (25)..(25)
<223> OTHER INFORMATION: fluroinated, Aptamer against protein region of
      Plasmodium falciparum
<220> FEATURE:
<221> NAME/KEY: misc_feature
<222> LOCATION: (26)..(26)
<223> OTHER INFORMATION: fluroinated, Aptamer against protein region of
      Plasmodium falciparum
```

```
<220> FEATURE:
<221> NAME/KEY: misc_feature
<222> LOCATION: (27)..(27)
<223> OTHER INFORMATION: fluroinated, Aptamer against protein region of
      Plasmodium falciparum
<220> FEATURE:
<221> NAME/KEY: misc_feature
<222> LOCATION: (30)..(30)
<223> OTHER INFORMATION: fluroinated, Aptamer against protein region of
      Plasmodium falciparum
<220> FEATURE:
<221> NAME/KEY: misc_feature
<222> LOCATION: (31)..(31)
<223> OTHER INFORMATION: fluroinated, Aptamer against protein region of
      Plasmodium falciparum
<220> FEATURE:
<221> NAME/KEY: misc_feature
<222> LOCATION: (32)..(32)
<223> OTHER INFORMATION: fluroinated, Aptamer against protein region of
      Plasmodium falciparum
<220> FEATURE:
<221> NAME/KEY: misc_feature
<222> LOCATION: (34)..(34)
<223> OTHER INFORMATION: fluroinated, Aptamer against protein region of
      Plasmodium falciparum
<220> FEATURE:
<221> NAME/KEY: misc_feature
<222> LOCATION: (35)..(35)
<223> OTHER INFORMATION: fluroinated, Aptamer against protein region of
      Plasmodium falciparum
<220> FEATURE:
<221> NAME/KEY: misc_feature
<222> LOCATION: (36)..(36)
<223> OTHER INFORMATION: fluroinated, Aptamer against protein region of
      Plasmodium falciparum
<220> FEATURE:
<221> NAME/KEY: misc_feature
<222> LOCATION: (38)..(38)
<223> OTHER INFORMATION: fluroinated, Aptamer against protein region of
      Plasmodium falciparum
<220> FEATURE:
<221> NAME/KEY: misc_feature
<222> LOCATION: (39)..(39)
<223> OTHER INFORMATION: fluroinated, Aptamer against protein region of
      Plasmodium falciparum
<220> FEATURE:
<221> NAME/KEY: misc_feature
<222> LOCATION: (40)..(40)
<223> OTHER INFORMATION: fluroinated, Aptamer against protein region of
      Plasmodium falciparum
<220> FEATURE:
<221> NAME/KEY: misc_feature
<222> LOCATION: (42)..(42)
<223> OTHER INFORMATION: fluroinated, Aptamer against protein region of
      Plasmodium falciparum
<220> FEATURE:
<221> NAME/KEY: misc_feature
<222> LOCATION: (44)..(44)
<223> OTHER INFORMATION: fluroinated, Aptamer against protein region of
      Plasmodium falciparum
<220> FEATURE:
<221> NAME/KEY: misc_feature
<222> LOCATION: (47)..(47)
<223> OTHER INFORMATION: fluroinated, Aptamer against protein region of
      Plasmodium falciparum
<220> FEATURE:
<221> NAME/KEY: misc_feature
<222> LOCATION: (48)..(48)
<223> OTHER INFORMATION: fluroinated, Aptamer against protein region of
      Plasmodium falciparum
<220> FEATURE:
<221> NAME/KEY: misc_feature
<222> LOCATION: (50)..(50)
<223> OTHER INFORMATION: fluroinated, Aptamer against protein region of
      Plasmodium falciparum
```

```
<220> FEATURE:
<221> NAME/KEY: misc_feature
<222> LOCATION: (53)..(53)
<223> OTHER INFORMATION: fluroinated, Aptamer against protein region of
      Plasmodium falciparum

<400> SEQUENCE: 9
cuucgaacgg cccugguugu ugguuuuaau ucauuuaucc gcguggucac ggu           53

<210> SEQ ID NO 10
<211> LENGTH: 50
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: fluroinated, Aptamer against protein region of
      Plasmodium falciparum
<220> FEATURE:
<221> NAME/KEY: misc_feature
<222> LOCATION: (4)..(4)
<223> OTHER INFORMATION: fluroinated, Aptamer against protein region of
      Plasmodium falciparum
<220> FEATURE:
<221> NAME/KEY: misc_feature
<222> LOCATION: (5)..(5)
<223> OTHER INFORMATION: fluroinated, Aptamer against protein region of
      Plasmodium falciparum
<220> FEATURE:
<221> NAME/KEY: misc_feature
<222> LOCATION: (6)..(6)
<223> OTHER INFORMATION: fluroinated, Aptamer against protein region of
      Plasmodium falciparum
<220> FEATURE:
<221> NAME/KEY: misc_feature
<222> LOCATION: (8)..(8)
<223> OTHER INFORMATION: fluroinated, Aptamer against protein region of
      Plasmodium falciparum
<220> FEATURE:
<221> NAME/KEY: misc_feature
<222> LOCATION: (9)..(9)
<223> OTHER INFORMATION: fluroinated, Aptamer against protein region of
      Plasmodium falciparum
<220> FEATURE:
<221> NAME/KEY: misc_feature
<222> LOCATION: (11)..(11)
<223> OTHER INFORMATION: fluroinated, Aptamer against protein region of
      Plasmodium falciparum
<220> FEATURE:
<221> NAME/KEY: misc_feature
<222> LOCATION: (13)..(13)
<223> OTHER INFORMATION: fluroinated, Aptamer against protein region of
      Plasmodium falciparum
<220> FEATURE:
<221> NAME/KEY: misc_feature
<222> LOCATION: (14)..(14)
<223> OTHER INFORMATION: fluroinated, Aptamer against protein region of
      Plasmodium falciparum
<220> FEATURE:
<221> NAME/KEY: misc_feature
<222> LOCATION: (17)..(17)
<223> OTHER INFORMATION: fluroinated, Aptamer against protein region of
      Plasmodium falciparum
<220> FEATURE:
<221> NAME/KEY: misc_feature
<222> LOCATION: (20)..(20)
<223> OTHER INFORMATION: fluroinated, Aptamer against protein region of
      Plasmodium falciparum
<220> FEATURE:
<221> NAME/KEY: misc_feature
<222> LOCATION: (21)..(21)
<223> OTHER INFORMATION: fluroinated, Aptamer against protein region of
      Plasmodium falciparum
```
<220> FEATURE:
<221> NAME/KEY: misc_feature
<222> LOCATION: (24)..(24)
<223> OTHER INFORMATION: fluroinated, Aptamer against protein region of Plasmodium falciparum
<220> FEATURE:
<221> NAME/KEY: misc_feature
<222> LOCATION: (26)..(26)
<223> OTHER INFORMATION: fluroinated, Aptamer against protein region of Plasmodium falciparum
<220> FEATURE:
<221> NAME/KEY: misc_feature
<222> LOCATION: (28)..(28)
<223> OTHER INFORMATION: fluroinated, Aptamer against protein region of Plasmodium falciparum
<220> FEATURE:
<221> NAME/KEY: misc_feature
<222> LOCATION: (29)..(29)
<223> OTHER INFORMATION: fluroinated, Aptamer against protein region of Plasmodium falciparum
<220> FEATURE:
<221> NAME/KEY: misc_feature
<222> LOCATION: (30)..(30)
<223> OTHER INFORMATION: fluroinated, Aptamer against protein region of Plasmodium falciparum
<220> FEATURE:
<221> NAME/KEY: misc_feature
<222> LOCATION: (31)..(31)
<223> OTHER INFORMATION: fluroinated, Aptamer against protein region of Plasmodium falciparum
<220> FEATURE:
<221> NAME/KEY: misc_feature
<222> LOCATION: (32)..(32)
<223> OTHER INFORMATION: fluroinated, Aptamer against protein region of Plasmodium falciparum
<220> FEATURE:
<221> NAME/KEY: misc_feature
<222> LOCATION: (33)..(33)
<223> OTHER INFORMATION: fluroinated, Aptamer against protein region of Plasmodium falciparum
<220> FEATURE:
<221> NAME/KEY: misc_feature
<222> LOCATION: (34)..(34)
<223> OTHER INFORMATION: fluroinated, Aptamer against protein region of Plasmodium falciparum
<220> FEATURE:
<221> NAME/KEY: misc_feature
<222> LOCATION: (38)..(38)
<223> OTHER INFORMATION: fluroinated, Aptamer against protein region of Plasmodium falciparum
<220> FEATURE:
<221> NAME/KEY: misc_feature
<222> LOCATION: (40)..(40)
<223> OTHER INFORMATION: fluroinated, Aptamer against protein region of Plasmodium falciparum
<220> FEATURE:
<221> NAME/KEY: misc_feature
<222> LOCATION: (41)..(41)
<223> OTHER INFORMATION: fluroinated, Aptamer against protein region of Plasmodium falciparum
<220> FEATURE:
<221> NAME/KEY: misc_feature
<222> LOCATION: (44)..(44)
<223> OTHER INFORMATION: fluroinated, Aptamer against protein region of Plasmodium falciparum
<220> FEATURE:
<221> NAME/KEY: misc_feature
<222> LOCATION: (46)..(46)
<223> OTHER INFORMATION: fluroinated, Aptamer against protein region of Plasmodium falciparum
<220> FEATURE:
<221> NAME/KEY: misc_feature
<222> LOCATION: (48)..(48)
<223> OTHER INFORMATION: fluroinated, Aptamer against protein region of Plasmodium falciparum

<400> SEQUENCE: 10
uagcucacca caccagcaau caacgcguuu uuucaaacac uggcacauga 50

```
<210> SEQ ID NO 11
<211> LENGTH: 50
<212> TYPE: RNA
<213> ORGANISM: Artificial Sequence
<220> FEATURE:
<221> NAME/KEY: misc_feature
<222> LOCATION: (3)..(3)
<223> OTHER INFORMATION: fluroinated, Aptamer against protein region of
      Plasmodium falciparum
<220> FEATURE:
<221> NAME/KEY: misc_feature
<222> LOCATION: (6)..(6)
<223> OTHER INFORMATION: fluroinated, Aptamer against protein region of
      Plasmodium falciparum
<220> FEATURE:
<221> NAME/KEY: misc_feature
<222> LOCATION: (8)..(8)
<223> OTHER INFORMATION: fluroinated, Aptamer against protein region of
      Plasmodium falciparum
<220> FEATURE:
<221> NAME/KEY: misc_feature
<222> LOCATION: (11)..(11)
<223> OTHER INFORMATION: fluroinated, Aptamer against protein region of
      Plasmodium falciparum
<220> FEATURE:
<221> NAME/KEY: misc_feature
<222> LOCATION: (12)..(12)
<223> OTHER INFORMATION: fluroinated, Aptamer against protein region of
      Plasmodium falciparum
<220> FEATURE:
<221> NAME/KEY: misc_feature
<222> LOCATION: (14)..(14)
<223> OTHER INFORMATION: fluroinated, Aptamer against protein region of
      Plasmodium falciparum
<220> FEATURE:
<221> NAME/KEY: misc_feature
<222> LOCATION: (16)..(16)
<223> OTHER INFORMATION: fluroinated, Aptamer against protein region of
      Plasmodium falciparum
<220> FEATURE:
<221> NAME/KEY: misc_feature
<222> LOCATION: (17)..(17)
<223> OTHER INFORMATION: fluroinated, Aptamer against protein region of
      Plasmodium falciparum
<220> FEATURE:
<221> NAME/KEY: misc_feature
<222> LOCATION: (19)..(19)
<223> OTHER INFORMATION: fluroinated, Aptamer against protein region of
      Plasmodium falciparum
<220> FEATURE:
<221> NAME/KEY: misc_feature
<222> LOCATION: (20)..(20)
<223> OTHER INFORMATION: fluroinated, Aptamer against protein region of
      Plasmodium falciparum
<220> FEATURE:
<221> NAME/KEY: misc_feature
<222> LOCATION: (26)..(26)
<223> OTHER INFORMATION: fluroinated, Aptamer against protein region of
      Plasmodium falciparum
<220> FEATURE:
<221> NAME/KEY: misc_feature
<222> LOCATION: (28)..(28)
<223> OTHER INFORMATION: fluroinated, Aptamer against protein region of
      Plasmodium falciparum
<220> FEATURE:
<221> NAME/KEY: misc_feature
<222> LOCATION: (29)..(29)
<223> OTHER INFORMATION: fluroinated, Aptamer against protein region of
      Plasmodium falciparum
<220> FEATURE:
<221> NAME/KEY: misc_feature
<222> LOCATION: (31)..(31)
<223> OTHER INFORMATION: fluroinated, Aptamer against protein region of
      Plasmodium falciparum
<220> FEATURE:
<221> NAME/KEY: misc_feature
<222> LOCATION: (32)..(32)
<223> OTHER INFORMATION: fluroinated, Aptamer against protein region of
      Plasmodium falciparum
```

-continued

<220> FEATURE:
<221> NAME/KEY: misc_feature
<222> LOCATION: (33)..(33)
<223> OTHER INFORMATION: fluroinated, Aptamer against protein region of
      Plasmodium falciparum
<220> FEATURE:
<221> NAME/KEY: misc_feature
<222> LOCATION: (34)..(34)
<223> OTHER INFORMATION: fluroinated, Aptamer against protein region of
      Plasmodium falciparum
<220> FEATURE:
<221> NAME/KEY: misc_feature
<222> LOCATION: (36)..(36)
<223> OTHER INFORMATION: fluroinated, Aptamer against protein region of
      Plasmodium falciparum
<220> FEATURE:
<221> NAME/KEY: misc_feature
<222> LOCATION: (38)..(38)
<223> OTHER INFORMATION: fluroinated, Aptamer against protein region of
      Plasmodium falciparum
<220> FEATURE:
<221> NAME/KEY: misc_feature
<222> LOCATION: (39)..(39)
<223> OTHER INFORMATION: fluroinated, Aptamer against protein region of
      Plasmodium falciparum
<220> FEATURE:
<221> NAME/KEY: misc_feature
<222> LOCATION: (45)..(45)
<223> OTHER INFORMATION: fluroinated, Aptamer against protein region of
      Plasmodium falciparum
<220> FEATURE:
<221> NAME/KEY: misc_feature
<222> LOCATION: (46)..(46)
<223> OTHER INFORMATION: fluroinated, Aptamer against protein region of
      Plasmodium falciparum
<220> FEATURE:
<221> NAME/KEY: misc_feature
<222> LOCATION: (49)..(49)
<223> OTHER INFORMATION: fluroinated, Aptamer against protein region of
      Plasmodium falciparum

<400> SEQUENCE: 11
aacaauacga cuacaccauc aaaaguauua ucuugcaucg aagguuggca                  50

<210> SEQ ID NO 12
<211> LENGTH: 65
<212> TYPE: RNA
<213> ORGANISM: Artificial Sequence
<220> FEATURE:
<221> NAME/KEY: misc_feature
<222> LOCATION: (2)..(2)
<223> OTHER INFORMATION: fluroinated, Aptamer against protein region of
      Plasmodium falciparum
<220> FEATURE:
<221> NAME/KEY: misc_feature
<222> LOCATION: (5)..(5)
<223> OTHER INFORMATION: fluroinated, Aptamer against protein region of
      Plasmodium falciparum
<220> FEATURE:
<221> NAME/KEY: misc_feature
<222> LOCATION: (6)..(6)
<223> OTHER INFORMATION: fluroinated, Aptamer against protein region of
      Plasmodium falciparum
<220> FEATURE:
<221> NAME/KEY: misc_feature
<222> LOCATION: (8)..(8)
<223> OTHER INFORMATION: fluroinated, Aptamer against protein region of
      Plasmodium falciparum
<220> FEATURE:
<221> NAME/KEY: misc_feature
<222> LOCATION: (10)..(10)
<223> OTHER INFORMATION: fluroinated, Aptamer against protein region of
      Plasmodium falciparum -continued <220> FEATURE:
<221> NAME/KEY: misc_feature
<222> LOCATION: (14)..(14)
<223> OTHER INFORMATION: fluroinated, Aptamer against protein region of
Plasmodium falciparum
<220> FEATURE:
<221> NAME/KEY: misc_feature
<222> LOCATION: (18)..(18)
<223> OTHER INFORMATION: fluroinated, Aptamer against protein region of
Plasmodium falciparum
<220> FEATURE:
<221> NAME/KEY: misc_feature
<222> LOCATION: (22)..(22)
<223> OTHER INFORMATION: fluroinated, Aptamer against protein region of
Plasmodium falciparum
<220> FEATURE:
<221> NAME/KEY: misc_feature
<222> LOCATION: (23)..(23)
<223> OTHER INFORMATION: fluroinated, Aptamer against protein region of
Plasmodium falciparum
<220> FEATURE:
<221> NAME/KEY: misc_feature
<222> LOCATION: (29)..(29)
<223> OTHER INFORMATION: fluroinated, Aptamer against protein region of
Plasmodium falciparum
<220> FEATURE:
<221> NAME/KEY: misc_feature
<222> LOCATION: (32)..(32)
<223> OTHER INFORMATION: fluroinated, Aptamer against protein region of
Plasmodium falciparum
<220> FEATURE:
<221> NAME/KEY: misc_feature
<222> LOCATION: (35)..(35)
<223> OTHER INFORMATION: fluroinated, Aptamer against protein region of
Plasmodium falciparum
<220> FEATURE:
<221> NAME/KEY: misc_feature
<222> LOCATION: (36)..(36)
<223> OTHER INFORMATION: fluroinated, Aptamer against protein region of
Plasmodium falciparum
<220> FEATURE:
<221> NAME/KEY: misc_feature
<222> LOCATION: (41)..(41)
<223> OTHER INFORMATION: fluroinated, Aptamer against protein region of
Plasmodium falciparum
<220> FEATURE:
<221> NAME/KEY: misc_feature
<222> LOCATION: (42)..(42)
<223> OTHER INFORMATION: fluroinated, Aptamer against protein region of
Plasmodium falciparum
<220> FEATURE:
<221> NAME/KEY: misc_feature
<222> LOCATION: (44)..(44)
<223> OTHER INFORMATION: fluroinated, Aptamer against protein region of
Plasmodium falciparum
<220> FEATURE:
<221> NAME/KEY: misc_feature
<222> LOCATION: (45)..(45)
<223> OTHER INFORMATION: fluroinated, Aptamer against protein region of
Plasmodium falciparum
<220> FEATURE:
<221> NAME/KEY: misc_feature
<222> LOCATION: (46)..(46)
<223> OTHER INFORMATION: fluroinated, Aptamer against protein region of
Plasmodium falciparum
<220> FEATURE:
<221> NAME/KEY: misc_feature
<222> LOCATION: (49)..(49)
<223> OTHER INFORMATION: fluroinated, Aptamer against protein region of
Plasmodium falciparum
<220> FEATURE:
<221> NAME/KEY: misc_feature
<222> LOCATION: (50)..(50)
<223> OTHER INFORMATION: fluroinated, Aptamer against protein region of
Plasmodium falciparum

```
<220> FEATURE:
<221> NAME/KEY: misc_feature
<222> LOCATION: (52)..(52)
<223> OTHER INFORMATION: fluroinated, Aptamer against protein region of
      Plasmodium falciparum
<220> FEATURE:
<221> NAME/KEY: misc_feature
<222> LOCATION: (54)..(54)
<223> OTHER INFORMATION: fluroinated, Aptamer against protein region of
      Plasmodium falciparum
<220> FEATURE:
<221> NAME/KEY: misc_feature
<222> LOCATION: (55)..(55)
<223> OTHER INFORMATION: fluroinated, Aptamer against protein region of
      Plasmodium falciparum
<220> FEATURE:
<221> NAME/KEY: misc_feature
<222> LOCATION: (58)..(58)
<223> OTHER INFORMATION: fluroinated, Aptamer against protein region of
      Plasmodium falciparum
<220> FEATURE:
<221> NAME/KEY: misc_feature
<222> LOCATION: (59)..(59)
<223> OTHER INFORMATION: fluroinated, Aptamer against protein region of
      Plasmodium falciparum
<220> FEATURE:
<221> NAME/KEY: misc_feature
<222> LOCATION: (61)..(61)
<223> OTHER INFORMATION: fluroinated, Aptamer against protein region of
      Plasmodium falciparum
<220> FEATURE:
<221> NAME/KEY: misc_feature
<222> LOCATION: (62)..(62)
<223> OTHER INFORMATION: fluroinated, Aptamer against protein region of
      Plasmodium falciparum
<220> FEATURE:
<221> NAME/KEY: misc_feature
<222> LOCATION: (63)..(63)
<223> OTHER INFORMATION: fluroinated, Aptamer against protein region of
      Plasmodium falciparum
<220> FEATURE:
<221> NAME/KEY: misc_feature
<222> LOCATION: (64)..(64)
<223> OTHER INFORMATION: fluroinated, Aptamer against protein region of
      Plasmodium falciparum

<400> SEQUENCE: 12
gugaccacgc ggauaaauga aucaaaaaca acaaccaggg ccguucgacu acgcuaauua      60
ucccg                                                                 65

<210> SEQ ID NO 13
<211> LENGTH: 20
<212> TYPE: DNA
<213> ORGANISM: Artificial Sequence
<220> FEATURE:
<223> OTHER INFORMATION: Consensus sequence in clones

<400> SEQUENCE: 13
gactgattac gccagcttgg                                                 20

<210> SEQ ID NO 14
<211> LENGTH: 20
<212> TYPE: DNA
<213> ORGANISM: Artificial Sequence
<220> FEATURE:
<223> OTHER INFORMATION: Consensus sequence in clones

<400> SEQUENCE: 14
cacactggcg gccgctcgag                                                 20
```

```
<210> SEQ ID NO 15
<211> LENGTH: 15
<212> TYPE: DNA
<213> ORGANISM: Artificial Sequence
<220> FEATURE:
<223> OTHER INFORMATION: Consensus sequence in clones

<400> SEQUENCE: 15
aattcgccct tgccg                                                         15

<210> SEQ ID NO 16
<211> LENGTH: 19
<212> TYPE: DNA
<213> ORGANISM: Artificial Sequence
<220> FEATURE:
<223> OTHER INFORMATION: Consensus sequence in clones

<400> SEQUENCE: 16
agctcggatc cactaataa                                                     19

<210> SEQ ID NO 17
<211> LENGTH: 19
<212> TYPE: DNA
<213> ORGANISM: Artificial Sequence
<220> FEATURE:
<223> OTHER INFORMATION: Consensus sequence in clones

<400> SEQUENCE: 17
gttgttggtt tggcttgtt                                                     19

<210> SEQ ID NO 18
<211> LENGTH: 15
<212> TYPE: DNA
<213> ORGANISM: Artificial Sequence
<220> FEATURE:
<223> OTHER INFORMATION: Consensus sequence in clones

<400> SEQUENCE: 18
aacaccaaca ccaac                                                         15

<210> SEQ ID NO 19
<211> LENGTH: 90
<212> TYPE: DNA
<213> ORGANISM: Artificial Sequence
<220> FEATURE:
<223> OTHER INFORMATION: Consensus sequence in clones
<220> FEATURE:
<221> NAME/KEY: misc_feature
<222> LOCATION: (21)..(71)
<223> OTHER INFORMATION: primer; positions 21-71 correspond to a central
      sequence of 50 randomised nucleotides

<400> SEQUENCE: 19
cgactgcaga gcttgctacg nnnnnnnnnn nnnnnnnnnn nnnnnnnnnn nnnnnnnnnn         60
nnnnnnnnnn ggtaccgagc tcgaattccc                                         90

<210> SEQ ID NO 20
<211> LENGTH: 40
<212> TYPE: DNA
<213> ORGANISM: Artificial Sequence
<220> FEATURE:
<221> NAME/KEY: misc_feature
<222> LOCATION: (4)..(21)
<223> OTHER INFORMATION: primer; sequence for T7 promotor

<400> SEQUENCE: 20
gcgtaatacg actcactata gggaattcga gctcggtacc                              40
```

```
<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cgactgcaga gcttgctacg                                              20

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gcgtaatacg actcactata g                                            21

<210> SEQ ID NO 23
<211> LENGTH: 20
<212> TYPE: DNA
<213> ORGANISM: Artificial Sequence
<220> FEATURE:
<223> OTHER INFORMATION: Aptamer against a region of a protein of
      Plasmodium falciparum

<400> SEQUENCE: 23
gacugauuac gccagcuugg                                              20

<210> SEQ ID NO 24
<211> LENGTH: 20
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: fluorinated, Aptamer against a region of a
      protein of Plasmodium falciparum
<220> FEATURE:
<221> NAME/KEY: misc_feature
<222> LOCATION: (4)..(4)
<223> OTHER INFORMATION: fluorinated, Aptamer against a region of a
      protein of Plasmodium falciparum
<220> FEATURE:
<221> NAME/KEY: misc_feature
<222> LOCATION: (7)..(7)
<223> OTHER INFORMATION: fluorinated, Aptamer against a region of a
      protein of Plasmodium falciparum
<220> FEATURE:
<221> NAME/KEY: misc_feature
<222> LOCATION: (8)..(8)
<223> OTHER INFORMATION: fluorinated, Aptamer against a region of a
      protein of Plasmodium falciparum
<220> FEATURE:
<221> NAME/KEY: misc_feature
<222> LOCATION: (10)..(10)
<223> OTHER INFORMATION: fluorinated, Aptamer against a region of a
      protein of Plasmodium falciparum
<220> FEATURE:
<221> NAME/KEY: misc_feature
<222> LOCATION: (12)..(12)
<223> OTHER INFORMATION: fluorinated, Aptamer against a region of a
      protein of Plasmodium falciparum
<220> FEATURE:
<221> NAME/KEY: misc_feature
<222> LOCATION: (13)..(13)
<223> OTHER INFORMATION: fluorinated, Aptamer against a region of a
      protein of Plasmodium falciparum
```

```
<220> FEATURE:
<221> NAME/KEY: misc_feature
<222> LOCATION: (16)..(16)
<223> OTHER INFORMATION: fluorinated, Aptamer against a region of a
      protein of Plasmodium falciparum
<220> FEATURE:
<221> NAME/KEY: misc_feature
<222> LOCATION: (17)..(17)
<223> OTHER INFORMATION: fluorinated, Aptamer against a region of a
      protein of Plasmodium falciparum
<220> FEATURE:
<221> NAME/KEY: misc_feature
<222> LOCATION: (18)..(18)
<223> OTHER INFORMATION: fluorinated, Aptamer against a region of a
      protein of Plasmodium falciparum

<400> SEQUENCE: 24
gacugauuac gccagcuugg                                              20
```